United States Patent
Boursnell et al.

(10) Patent No.: US 6,287,557 B1
(45) Date of Patent: *Sep. 11, 2001

(54) METHODS OF GENE THERAPY USING HERPES VIRAL VECTORS EXPRESSING GM-CSF

(75) Inventors: Michael E. G. Boursnell; Stephen C. Inglis, both of Cambridge (GB)

(73) Assignee: Cantab Pharmaceuticals Research Limited, Cambridge (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/604,165

(22) Filed: Feb. 21, 1996

(30) Foreign Application Priority Data

| Feb. 21, 1995 | (GB) | 9503395 |
| Jul. 28, 1995 | (GB) | 9515557 |
| Feb. 16, 1996 | (GB) | 9603322 |

(51) Int. Cl.[7] .............. A61K 48/00; C12N 15/88

(52) U.S. Cl. .............. 424/93.2; 435/91.4; 435/91.41; 435/91.42; 435/320.1; 435/455

(58) Field of Search .............. 514/44; 435/235.1, 435/320.1, 325, 69.1, 91.41, 91.42, 455, 91.4; 424/93.21, 93.2; 935/57, 62, 71

(56) References Cited

U.S. PATENT DOCUMENTS

| 5,585,096 | * | 12/1996 | Martuza et al. | 424/93.21 |
| 5,637,483 | * | 6/1997 | Dranoff et al. | 424/93.21 |
| 5,658,724 | * | 8/1997 | DeLuca | 435/5 |
| 5,661,033 | * | 8/1997 | Ho et al. | 435/320.1 |
| 5,665,362 | * | 9/1997 | Inglis et al. | 424/205.1 |
| 5,837,261 | * | 11/1998 | Inglis et al. | 424/229.1 |

FOREIGN PATENT DOCUMENTS

| 0453242A1 | | 4/1991 | (EP) . |
| 0572978A1 | | 6/1993 | (EP) . |
| 90/10693 | | 9/1990 | (WO) . |
| 92/05263 | | 4/1992 | (WO) . |
| 94/03595 | | 2/1994 | (WO) . |
| WO 94/03207 | * | 2/1994 | (WO) . |
| WO 94/21807 | * | 9/1994 | (WO) . |
| 94/24296 | | 10/1994 | (WO) . |
| WO 94/29469 | * | 12/1994 | (WO) . |
| 95/03399 | | 2/1995 | (WO) . |

OTHER PUBLICATIONS

Robertson et al., Technology evaluation: DISC, 1999, Molecular Therapeutics, vol. 1, No. 1, p. 112–115.*
Verma et al., Gene therapy–promises, problems and prospects, Sep. 18, 1997, Nature, vol. 389, pp. 239–242.*
Jolly (Cancer Gene Ther., vol. 1, 1, pp. 51–64, 1994).*
Gunzburg et al., Molecular Medicine Today, 1, 1995, pp. 410–417*
Mastrangelo et al. (Seminars in Oncology, vol. 23, 1:4–21), 1996.*
Pardoll, TIPS, vol. 14: 202–208; 1993.*
Forrester, A et al. Construction and properties of a mutant of herpes simplex virus type 1 with glycoprotein H coding sequences deleted. J. Virol. 66:341–348, Jan. 1, 1992.*
Danos, O et al. Safe and efficient generation of recombinant retroviruses with amphotropic and ecotropic host ranges. Proc. Natl. Acad. Sci. USA 85:6460–6464, Sep. 1, 1988.*
Zitvogel, L et al. Construction and characterization of retroviral vectors expressing biologically active human interleukin–12. Human Gene Therapy 5:1493–1506, Dec. 1, 1994.*
Gansbacher, B et al. Retroviral vector–mediated interferon gene transfer into tumor cells generates potent and long lasting antitumor immunity. Cancer Res. 50:7820–7825, Dec. 15, 1990.*
Smith, GL et al. Infectious vaccinia virus recombinants that express hepatitis B surface antigen. Nature 302:490–495, Apr. 7, 1983.*
Bellone, M et al. In vitro priming of cytotoxic T lymphocytes against poorly immunogenic epitopes by engineered antigen–presenting cells. Eur. J. Immunol. 24:2691–2698, 1994.*
Farrell, H.E., et al., "Vaccine Potential of a Herpes Simplex Virus Type 1 Mutant with an Essential Glycoprotein Deleted," *Journal of Virology*, 68(2):927–932 (1994).
McLean, C.S., et al., "Protective Vaccination against Primary and Recurrent Disease Caused by Herpes Simplex Virus (HSV) Type 2 Using a Genetically Disabled HSV–1," *Journal of Infectious Diseases*, 170:1100–1109 (1994).

* cited by examiner

*Primary Examiner*—Dave Trong Nguyen
(74) *Attorney, Agent, or Firm*—Klarquist Sparkman Campbell Leigh & Whinston, LLP

(57) ABSTRACT

A genetically disabled mutant virus has a genome which is defective in respect of a selected gene that is essential for the production of infectious new virus particles, and which carries heterologous genetic material encoding an immunomodulatory protein such as GM-CSF, IL-2, or others, such that the mutant virus can infect normal host cells and cause expression of immunomodulatory protein, but the mutant virus cannot cause production of infectious new virus particles except when the virus infects recombinant complementing host cells expressing a gene that provides the function of the essential viral gene; the site of insertion of the heterologous genetic material encoding the immunomodulatory protein preferably being at the site of the defect in the selected essential viral gene. Uses include prophylactic and therapeutic use in generating an immune response in a subject treated therewith; use in the preparation of an immunogen such as a vaccine for use in tumor therapy; use in the in-vitro expansion of (e.g. virus-specific) cytotoxic T cells; and therapeutic or prophylactic use in corrective gene therapy.

5 Claims, 7 Drawing Sheets

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (iii) HYPOTHETICAL: NO (iii) ANTI-SENSE: NO (xi) SEQUENCE DESCRIPTION: SEQ ID NO: 1:

AGCTTAGTAC TGACGAC                           17

(2) INFORMATION FOR SEQ ID NO: 2:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (iii) HYPOTHETICAL: NO (iii) ANTI-SENSE: NO (xi) SEQUENCE DESCRIPTION: SEQ ID NO: 2:

CATGGTCGTC AGTACTA                                                                17

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 3:

GTGGAGACGC GAATAATCGC GAGC                                                        24

(2) INFORMATION FOR SEQ ID NO: 4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 4:

GGCCGCTCGC GATTATTCGC GTCTCCACAA AA                                               32

(2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 5:

TCGAAGCTTC AGGGAGTGGC GCAGC                                                       25

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 6:

TCAGTTAACG GACAGCATGG CCAGGTCAAG                                                  30

(2) INFORMATION FOR SEQ ID NO: 7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 7:

TCAGTTAACG CCTCTGTTCC TTTCCCTTC                                   29

(2) INFORMATION FOR SEQ ID NO: 8:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (iii) HYPOTHETICAL: NO (iii) ANTI-SENSE: NO (xi) SEQUENCE DESCRIPTION: SEQ ID NO: 8:

TCAGAATTCG AGCAGCTCCT CATGTTCGAC                                  30

(2) INFORMATION FOR SEQ ID NO: 9:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (iii) HYPOTHETICAL: NO (iii) ANTI-SENSE: NO (xi) SEQUENCE DESCRIPTION: SEQ ID NO: 9:

TCAGTTAACG CCTCTGTTCC TTTCCCTTC                                   29

(2) INFORMATION FOR SEQ ID NO: 10:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (iii) HYPOTHETICAL: NO (iii) ANTI-SENSE: NO (xi) SEQUENCE DESCRIPTION: SEQ ID NO: 10:

TCAGAATTCG TTCCGGGAGC AGGCGTGGA                                   29

(2) INFORMATION FOR SEQ ID NO: 11:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (iii) HYPOTHETICAL: NO (iii) ANTI-SENSE: NO (xi) SEQUENCE DESCRIPTION: SEQ ID NO: 11:

TCAAAGCTTA TGGCTTCTCA CGCCGGCCAA                                  30

(2) INFORMATION FOR SEQ ID NO: 12:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (iii) HYPOTHETICAL: NO (iii) ANTI-SENSE: NO (xi) SEQUENCE DESCRIPTION: SEQ ID NO: 12:

TCAGTTAACT GCACTAGTTT TAATTAATAC GTATG                               35

(2) INFORMATION FOR SEQ ID NO: 13:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 13:

TGGATGACAT GCCTGTCACA TTGAATGAAG AGGTAGAAGT                          40

(2) INFORMATION FOR SEQ ID NO: 14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 14:

GGCCGCTCGA ACATGGCCCA CGAGAGAAAG GCTAAG                              36

(2) INFORMATION FOR SEQ ID NO: 15:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 15:

GACCTTAGCC TTTCTCTCGT GGGCCATGTT CGAGC                               35

(2) INFORMATION FOR SEQ ID NO: 16:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 16:

```
TTAATACGAC TCACTATAGG GAGACCGGAA GCTTGGTACC GAGCTCGGAT CCACTAGTAA      60

CGGCCGCCAG TGTGCTGGAA TTCTGCAGAT ATCCATCACA CTGGCGGCCG CTCGAGCATG     120

CATCTAGCCT TTTGACTACA ATGGCCCACG AGAGAAAGGC TAAGGTCCTG               170
```

(2) INFORMATION FOR SEQ ID NO: 17:

(i) SEQUENCE CHARACTERISTICS:
        (A) LENGTH: 147 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 17:

```
TTAATACGAC TCACTATAGG GAGACCGGAA GCTTGGTACC GAGCTCGGAT CCACTAGTAA      60

CGGCCGCCAG TGTGCTGGAA TTCTGCAGAT ATCCATCACA CTGGCGGCCG CTCGAACATG     120

GCCCACGAGA GAAAGGCTAA GGTCCTG                                        147
```

(2) INFORMATION FOR SEQ ID NO: 18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 18:

```
TCGAAGCTTC AGGGAGTGGC GCAGC                                           25
```

(2) INFORMATION FOR SEQ ID NO: 19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 19:

```
TCAGTTAACG GCCAGCATAG CCAGGTCAAG                                      30
```

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 20:

```
TCAGTTAACA GCCCCTCTTT GCTTTCCCTC                                      30
```

(2) INFORMATION FOR SEQ ID NO: 21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 21:

TCAGAATTCG AGCAGCTCCT CATGTTCGAC                                              30

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 22:

TCAAAGCTTA TGGCTTCGTA CCCCTGCCAT                                              30

(2) INFORMATION FOR SEQ ID NO: 23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 23:

TCAGTTAACG GACCCCGTCC CTAACCCACG                                              30

(2) INFORMATION FOR SEQ ID NO: 24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iii) ANTI-SENSE: NO (xi) SEQUENCE DESCRIPTION: SEQ ID NO: 24:

TCAGTTAACA GCCCCTCTTT GCTTTCCCTC                                              30

(2) INFORMATION FOR SEQ ID NO: 25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO

```
        -continued (iii) ANTI-SENSE: NO (xi) SEQUENCE DESCRIPTION: SEQ ID NO: 25:

TCAGAATTCG AGCAGCTCCT CATGTTCGAC                                         30
```

METHODS OF GENE THERAPY USING HERPES VIRAL VECTORS EXPRESSING GM-CSF

This invention relates to viral preparations, immunogens, vaccines and immunotherapeutic agents, and in particular to mutant viruses, their culture, vaccines, and their preparation and uses, e.g. as vectors for evoking immune responses or for corrective gene therapy.

BACKGROUND AND PRIOR ART

Attenuated live viruses, including genetically engineered recombinants, are known as useful vaccine vectors. The genome of the live virus can be engineered to carry genes encoding heterologous antigens against which immunological responses are desired in such a way that the replicative ability of the live virus is preserved, and that the heterologous gene is expressed in cells infected by the recombinant virus. The expressed antigens are thus available to provoke a useful immune response. The heterologous antigens may originate from an infectious pathogen, in order that a protective or therapeutic immune response can be mounted against the infectious agent, but alternatively they may represent tumour cell-specific or tumour-associated antigens; here the aim is to induce an immune response against tumour cells, to induce tumour rejection or regression.

More generally, recombinant viral vectors are among several known agents available for the introduction of foreign genes into cells so that they can be expressed as protein. A central element is the target gene itself under the control of a suitable promoter sequence that can function in the cell to be transduced. Known techniques include non-viral methods, such as simple addition of the target gene construct as free DNA; incubation with complexes of target DNA and specific proteins designed for uptake of the DNA into the target cell; and incubation with target DNA encapsulated e.g. in liposomes or other lipid-based transfection agents.

A further option is the use of recombinant virus vectors engineered to contain the required target gene, and able to infect the target cells and hence carry into the cell the target gene in a form that can be expressed. A number of different viruses have been used for this purpose including retroviruses, adenoviruses, and adeno-associated viruses.

Specification EP 0 176 170 (Institut Merieux: B Roizman) describes foreign genese inserted into a herpes simplex viral genome under the control of promote- regulatory regions of the genome, thus providing a vector for the expression of the foreign gene. DNA constructs, plasmid vectors containing the constructs useful for expression of the foreign gene, recombinant viruses produced with the vector, and associated methods are disclosed.

Specifications EP 0 448 650 (General Hospital Corporation: AI Geller, XO Breakefield) describes herpes simplex virus type 1 expression vectors capable of infecting and being propagated in a non-mitotic cell, and for use in treatment or neurological diseases, and to produce animal and in vitro models of such diseases.

Recombinant viruses are known in particular for use in gene therapy applied to gene deficiency conditions.

Examples of genes used or proposed to be used in gene therapy include: the gene for human adenosine deaminase (ADA), as mentioned in for example WO 92/10564 (KW Culver et al: US Secretary for Commerce & Cellco Inc), WO 89/12109 & EP 0 420 911 (IH Pastan et al); the cystic fibrosis gene and variants described in WO 91/02796 (L-C Tsui et al: HSC Research & University of Michigan), in WO 92/05273 (FS Collins & JM Wilson: University of Michigan) and in WO 94/12649 (RJ Gregory et al: Genzyme Corp).

The prior art of malignant tumour treatment includes studies that have highlighted the potential for therapeutic vaccination against tumours using autologous material derived from a patient's own tumour. The general theory behind this approach is that tumour cells may express one or more proteins or other biological macromolecules that are distinct from normal healthy cells, and which might therefore be used to target an immune response to recognise and destroy the tumour cells.

These tumour targets may be present ubiquitously in tumours of a certain type. A good example of this in cervical cancer, where the great majority of tumours express the human papillomavirus E6 E7 proteins. In this case the tumour target is not a self protein, and hence its potential as a unique tumour-specific marker for cancer immunotherapy is clear.

There is increasing evidence that certain self proteins can also be used as tumour target antigens. This is based on the observation that they are expressed consistently in tumour cells, but not in normal healthy cells. Examples of these include the MAGE family of proteins. It is expected that more self proteins useful as tumour targets remain to be identified.

Tumour associated antigens and their role in the immunobiology of certain cancers are discussed for example by P van der Bruggen et al, in Current Opinion in Immunology, 4(5) (1992) 608–612. Other such antigens, of the MAGE series, are identified in T. Boon, Adv Cancer Res 58 (1992) pp 177–210, MZ2-E and other related tumour antigens are identified in P. van der Bruggen et al, Science 254 (1991) 1643–1647; tumour associated mucins are mentioned in PO Livingston, in current Opinion in Immunology 4 (5) (1992) pp 624–629; e.g. MUCl as mentioned in J Burchell et al, Int J Cancer 44 (1989) pp 691–696.

Although some potentially useful tumour-specific markers have thus been identified and characterised, the search for new and perhaps more specific markers is laborious and time-consuming, and with no guarantee of success.

Administration to mammals of cytokines as such has been tried, but is often poorly tolerated by the host and is frequently associated with a number of side-effects including nausea, bone pain and fever. (A Mire-Sluis, TIBTech vol. 11 (1993); MS Moore, in Ann Rev Immunol 9 (1991) 159–91). These problems are exacerbated by the dose levels after required to maintain effective plasma concentrations.

Virus vectors have been proposed for use in cancer immunotherapy to provide a means for enhancing tumour immunoresponsiveness.

It is known to modify live virus vectors to contain genes encoding a cytokine or tumour antigen: see specification WO 94/16716 (E Paoletti et al: Virogentics Corp.) and reference cited therein: WO 94/16716 describes, for use in cancer therapy, attenuated recombinant vaccinia viruses containing DNA coding for a cytokine or a tumour antigen. Cytokines are examples of immunomodulating proteins. Immuno-modulating proteins which enhance the immune response such as the cytokine, interleukin 1, interleukin 2 and granulocyte-macrophage colony stimulating factor (GM-CSF) (see for example A W Heath et al., Vaccine 10 (7) (1992), and Tao Mi-Hua et al., Nature 362 (1993)), can be effective vaccine adjuvants.

It has been proposed to use GMCSF-transduced tumour cells as a therapeutic vaccine against renal cancer. The protocols for corresponding trials involve removal of tumour material from the patients, and then transduction with the appropriate immunomodulator gene. The engineered cells are then to be re-introduced into the patient to stimulate a beneficial immune response.

Although it has been proposed to introduce immunomodulatory genes into certain kinds of tumour cells, existing methods are considered to have limitations, whether the difficulties are due to low quantitative amounts of transduction, to complexity, or to undesirable side-effects of the systems employed.

Recently, an experimental intracranial murine melanoma has been described as treated with a neuroattenuated HSV1 mutant 1716 (BP Randazzo et al., Virology 211 (1995) pp94–101), of which the replication appeared to be restricted to tumour cells and not to occur on surrounding brain tissue.

Furthermore, vectors based on herpesvirus saimiri, a virus of non-human primates, have been described as leading to gene expression in human lymphoid cells (B Fleckenstein & R Grassmann, Gene 102(2) (1991), pp 265–9). However, it has been considered undesirable to use such vectors in a clinical setting.

The prior art includes specification WO 92/05263 (Inglis et al: Immunology Limited) (the content of which is incorporated herein by reference), which describes for example the use as vaccine of a mutant virus whose genome is defective in respect of a gene essential for the production of infectious virus, such that the virus can infect normal host cells and undergo replication and expression of viral antigen genes in such cells but cannot produce infectious virus. WO 92/05263 particularly describes an HSV virus which is disabled by the deletion of a gene encoding the essential glycoprotein H (gH) which is required for virus infectivity (A Forrester et al, J Virol 66 (1992) 341–348). In the absence of gH protein expression non-infectious virus particles providing almost the complete repertoire of viral proteins are produced. These progeny virus, however, are not able to infect host cells and spread of the virus within the host is prevented. Such a virus has been shown to be an effective vaccine in animal model systems (Farrell et al, J Virol 68 (1994) 927–932; McLean et al, J Infect Dis, 170 (1994) 1100–9). These mutants viruses can be cultured in a cell line which expresses the gene product in respect of which the mutant virus is defective. Cell lines which are suitable for the culture of certain viruses of this type have been described in the literature: for example in references given in cited specification WO 92/05263.

Complete or substantial sequence data has been published for several viruses such as Epstein-Barr virus EBV (Baer et al, in Nature 310 (1984) 207), human cytomegalovirus CMV (Weston and Barrell in J Mol Biol 192 (1986) 177–208), varicella zoster virus VZV (Davison and Scott, in J Gen Virol 67 (1986) 759–816) and herpes simplex virus HSV (McGeoch et al, in J. Gen. Virol. 69 (1988) 1531–1574). The gH glycoprotein is known to have homologues in EBV, CMV and VZV (Desai et al, in J Gen Virol 69 (1988) 1147).

Virus vectors provide an opportunity for intracellular delivery of both DNA and protein, for immunisation and gene therapy, e.g. corrective gene therapy, as well as for use in for example cancer immunotherapy, but the prior art leaves it still desirable to provide further viral vectors and processes useful for transforming human and non-human animal cells and expressing proteins therein.

BRIEF DESCRIPTION OF THE DRAWINGS

FIG. 7A is a diagram of the recombination of a virus carrying a foreign gene at the gH locus with a wildtype virus carrying a foreign gene at the gH locus. FIG. 7B is a diagram of the recombination of a virus carrying a foreign gene at the gH locus with a wild type gH gene.

DETAILED DESCRIPTION OF THE SPECIFIC EMBODIMENTS

Figure 1:
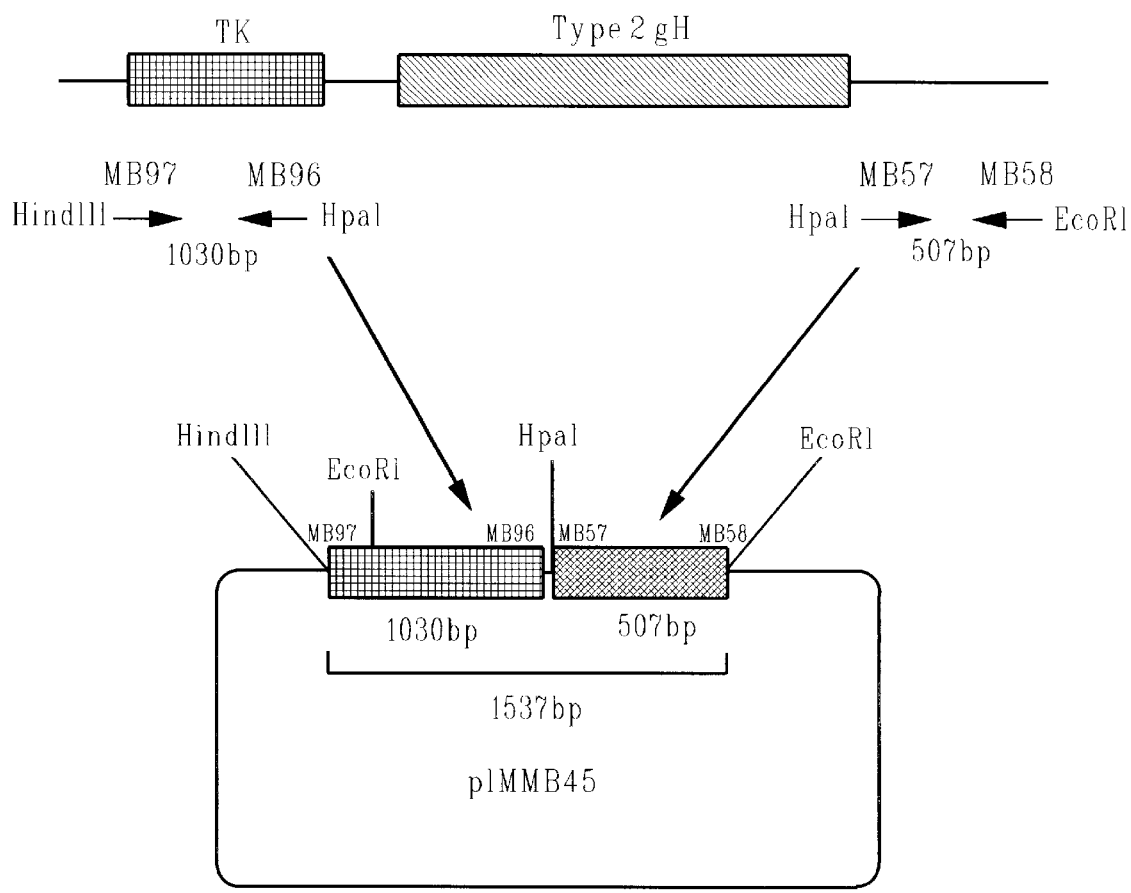
FIG. 1 is a diagram of the construction of plasmid pIMMB45.
Figure 2:
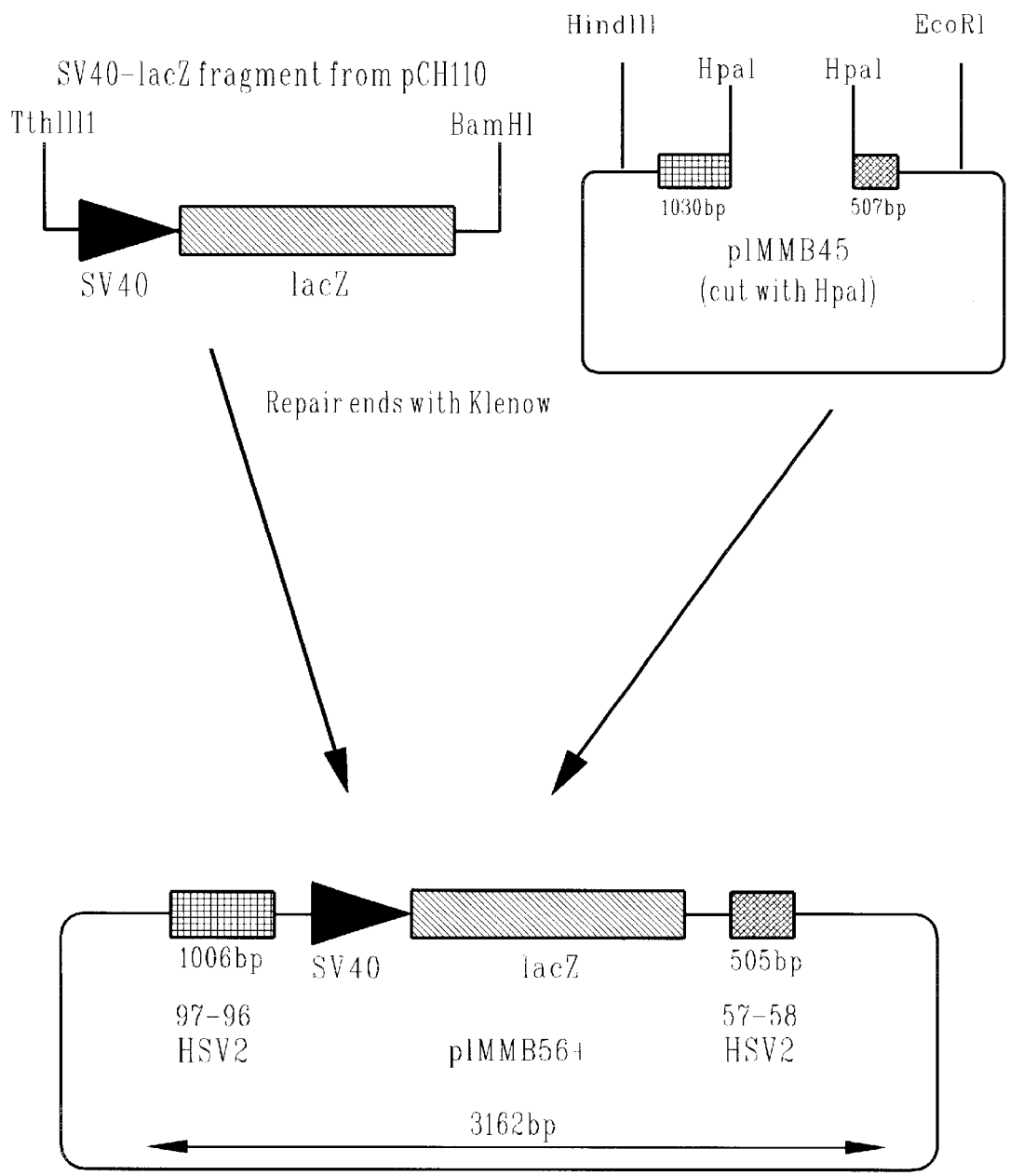
FIG. 2 is a diagram of the construction of plasmid pIMMB56.
Figure 3:
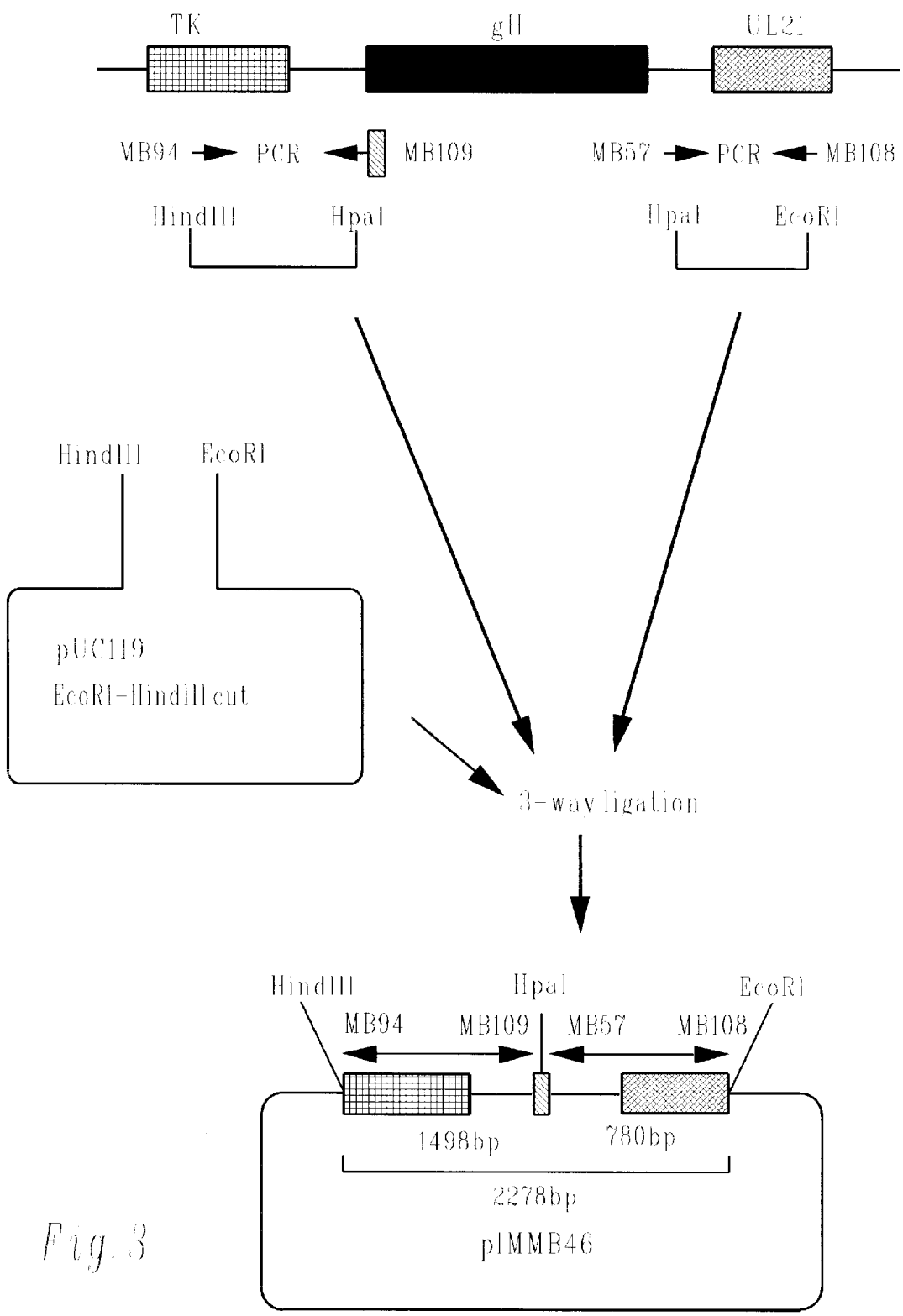
FIG. 3 is a diagram of the construction of the second stage recombination vector, pIMMB46.
Figure 4:
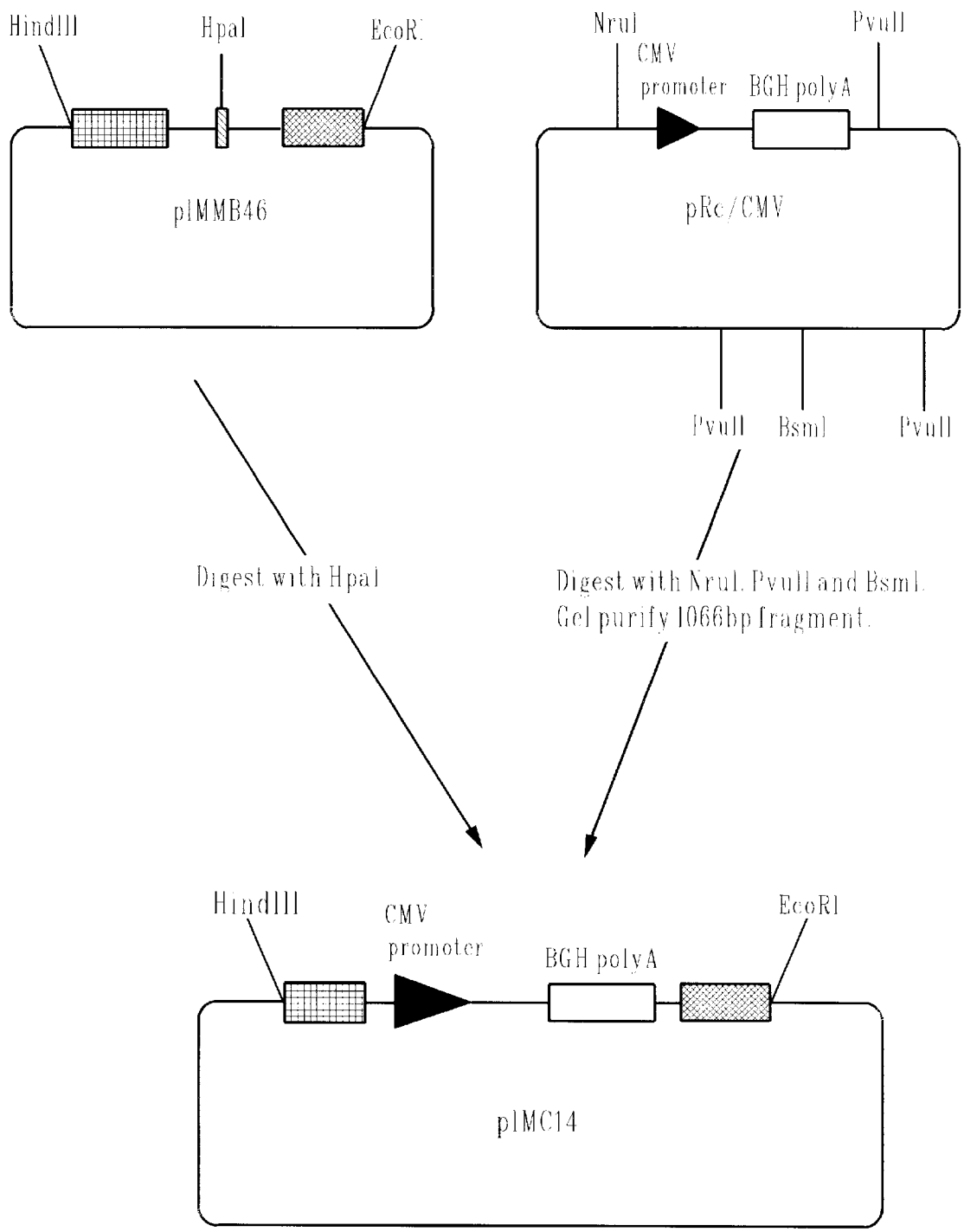
FIG. 4 is a diagram of the construction of pIMC14.
Figure 5:
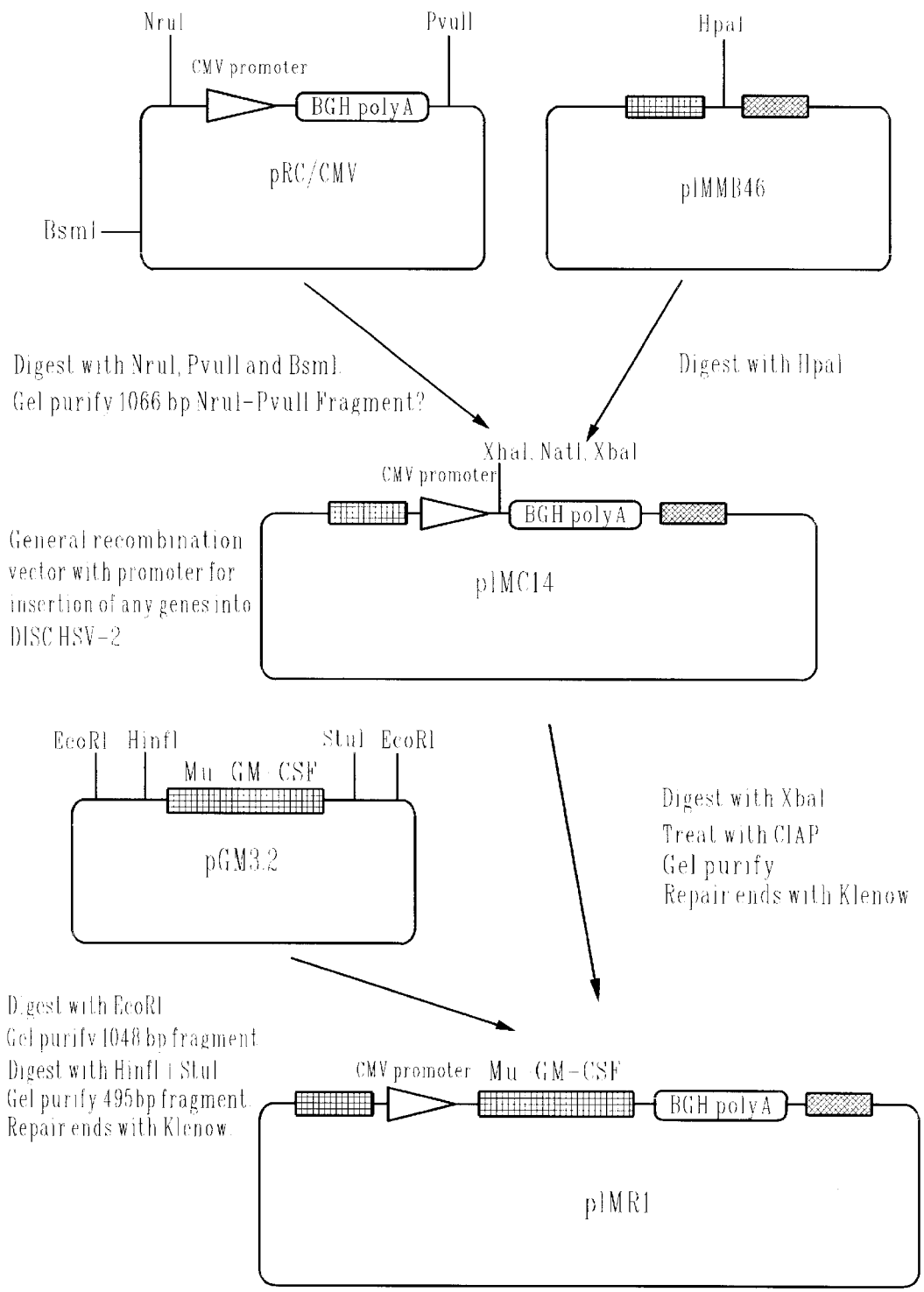
FIG. 5 is a diagram of the construction of plasmids for insertion of GM-CSF into HSV-2.
Figure 6:
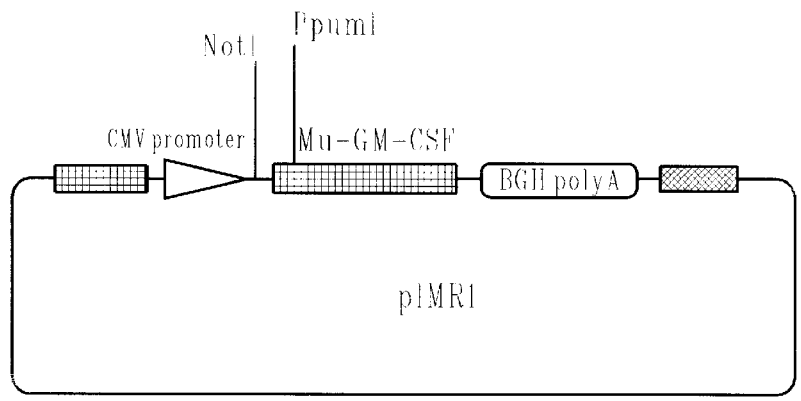
FIG. 6 is a diagram of the mutagenesis of plasmid pIMR1 to pIMR3.
Figure 6:
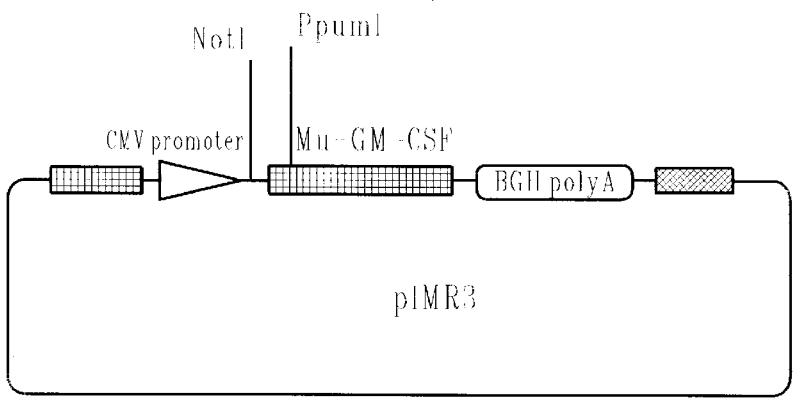

According to the present invention, as described in further detail below, a genetically inactivated (genetically disabled) mutant virus vaccine provides an useful carrier for genes encoding immunomodulatory proteins, and can be thus used as a virus vector. The virus vaccine can infect cells e.g. of a vaccinated subject leading to intracellular synthesis of viral antigens as well as of the immunomodulatory proteins. Thus the immune response to the virus can in certain examples of the invention be potentiated, whether it is made against viral-encoded antigens or in response to the immunomodulatory protein encoded by the virus. If the genetically inactivated vaccine is also acting as a vector for delivery of foreign antigens, then the immune response against the foreign antigen can also be enhanced.

Since the vaccine virus can undergo only a single cycle of replication in cells of the vaccinated host, however, production of the immunomodulatory proteins will be confined to the site of vaccination, in contrast to the situation with a replication competent virus, where infection might spread throughout the body. Furthermore, the overall amounts produced, though locally sufficient to stimulate a vigorous immune response, will be considerably less than that produced by a replication competent virus, and thus much less likely to produce adverse systemic responses.

It is considered an advantage to provide a vaccine or vector system with the immunological benefit of a live virus or virus vector together with the benefit of local production of immunodulatory protein, and which minimises the potential risk to the vaccinated subject of unforeseen pathology, also avoiding the potential environmental risk of allowing spread of the new and potentially harmful replicating pathogen.

Cytokine administration as such is often poorly tolerated by the host and is frequently associated with a number of side-effects including nausea, bone pain and fever. (A Mire-Sluis, TIBTech vol. 11 (1993); MS Moore, in Ann Rev Immunol 9 (1991) 159–91) These problems are exacerbated by the dose levels often required to maintain effective plasma concentrations. To reduce systemic toxicity a more targeted delivery of active cytokine is proposed, as described herein.

A previous approach to overcome this problem was to fuse antigen and cytokine genes to create a single bifunctional polypeptide (M Hazama et al, Vaccine 11 (1993) p6).

An alternative approach is to incorporate an nucleotide sequence encoding an immunomodulating protein into a live virus vaccine. Specification WO 94/16716 (E Paoletti et al: Virogenetics Corp.) describes attenuated recombinant vaccinia viruses containing DNA coding for cytokine or tumour antigen for use in cancer therapy.

Virus vectors have found application in cancer immunotherapy by providing a means for enhancing tumour immunoresponsiveness.

However, the present inventors consider that the use of live viruses to carry immunomodulatory genes can pose a risk to the community as well as the vaccinated individual. A vaccine virus which is unable to spread from cell to cell, as provided by the invention described herein, provides a considerable safety advantage, since in normal circumstances there can be no transmission to other individuals from the vaccines.

Figure 7:
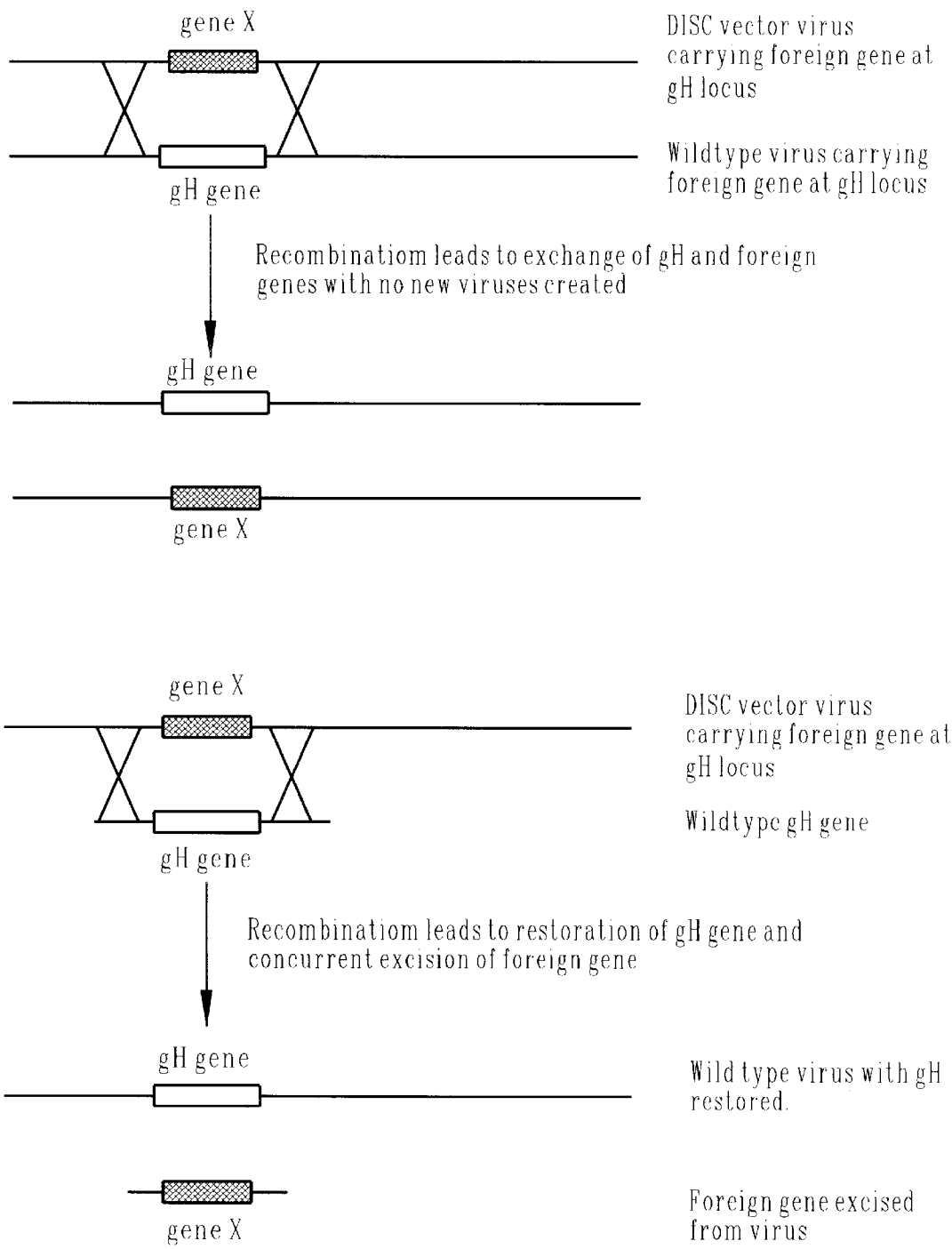
FIG. 7 is two diagrams of the recombination of a virus carrying a foreign gene at the gH locus.

One unusual circumstance in which a transmission risk could arise, however, is that if recombination were to occur between the genetically inactivated virus and a naturally occurring wild virus within the vaccine, transfer might occur of the immunomodulatory gene into the natural virus genome, or to the reconstitution of replication competence by the vaccine virus through acquisition of the missing gene. It is well known that homologous recombination between closely related viruses can occur at relatively high frequency when cells are simultaneously infected with both viruses. This potential capacity can however be avoided by ensuring, as is preferred according to the present disclosure, that the immunomodulatory gene is inserted at the point within the vaccine virus genome where the essential gene has been deleted. The consequence of this mode of construction is that homologous recombination with a wild virus, should it indeed occur within the vaccinated host, cannot result in the production of a new virus that is both replication competent and carries the immunomodulatory gene (FIG. 7 of the accompanying drawings). This is because the transfer of the deleted gene back into the vaccine virus would lead to loss of heterologous sequences inserted at that site. By the same token, transfer of the heterologous sequences to the wild virus would result in loss of an essential gene.

According to the present invention, therefore, there is provided a mutant virus which has a genome which is defective in respect of a first gene essential for the production of infectious virus, and which includes a heterologous nucleotide sequence which encodes an immunomodulating protein. Additionally, in certain embodiments the virus can also encode a heterologous antigen, e.g. a viral or non-viral, e.g. tumour antigen.

The mutant virus can be a mutant DNA or RNA virus e.g. a mutant non-retroviral virus, e.g. a RNA virus other than a retroviral virus) for example a mutant herpesvirus, adenovirus, papovavirus, or a mutant poxvirus. Mutant herpesviruses can for example be based on HSV1, HSV2, VZV, CMV, EBV, HHV6, HHV7, or on non-human animal herpesviruses such as PRV, IBRV/BHV, MDV, EHV, and others.

The genome of the mutant virus is defective in respect of a selected gene essential for the protection of infectious virus by infected host cells, such that the virus can infect normal host cells (i.e. cells other than those which have been mutated so that they express the product of the essential gene in respect of which the virus is defective) and cause viral replication and expression of viral antigen genes in those cells, but cannot cause production of normal infectious virus. In such a mutant virus the genetic defect can be such (e.g. deletion of herpesvirus gH or gD) as to allow the production and release of non-infectious viral particles when the mutant virus infects host cells other than such recombinant complementing host cells.

Thus the present invention provides a mutant virus whose genome is defective in respect of a gene essential for the production of infectious virus, such that the virus can infect normal cells and replicate therein to give rise to the production and release from the cells of non-infectious viral particles, and contains at least one heterologous nucleotide sequence which encodes at least one immunomodulating protein. A plurality of heterologous sequences can be carried in a single viral vector, encoding if desired a plurality of immunomodulating proteins. Alternatively, mixtures of vectors each containing a respective heterologous nucleic acid sequence encoding an immunomodulatory protein can be used.

The present invention also provides a mutant virus whose genome is defective in respect of a gene essential for the production of infectious virus and which carries genetic material encoding an immunogen or a plurality of immunogens from a pathogen exogenous to the virus, such that the virus can infect normal cells and undergo some replication and expression of the genetic material encoding the immunogen but cannot produce infectious virus particles, and contains a heterologous nucleotide sequence which encodes an immunomodulating protein.

As used herein, the expression "immunomodulatory protein" and related terms includes a protein or proteins which either enhance or suppress a host immune response to a mutant virus or protein encoded thereby, or to an antigen such as an immunogen from a pathogen or source exogenous to the virus, or a tumour-associated antigen. The immunomodulating proteins are not normally those proteins presently used as immunogens (antigens) in themselves. An immunomodulatory protein can be a natural member of a human or non-human animal immune system, e.g. of a mammalian immune system, with a functional binding capacity for another natural constituent of such an immune system. Alternatively an immunomodulatory protein can be a protein encoded by a pathogen, which has a functional binding capacity for a natural constituent of such an immune system. Alternatively an immunomodulatory protein can be an artificial protein, for example a fragment of a natural immunomodulatory protein, or a mutein of such a protein in fragment, or a fusion protein incorporating any of these. Many immunomodulatory proteins, and genetic materials encoding them, and their nucleotide and amino acid sequences, are known to the literature of this subject, and available in genetic sequence databases such as the EMBL database, and several are commercially available in the form of engineered genetic material for cloning and other manipulation.

Immunomodulating proteins for which encoding nucleotide sequences are expressibly carried by mutant virus vectors as described herein can usefully for example be of sequences native to the species which is to receive vaccination by the recombinant viruses e.g. an immunomodulating protein of human type for treatment of a human subject.

The protein(s) can be selected in certain examples of the invention to enhance the effect of the mutant virus as an immunogen, e.g. as a vaccine. Potential hazards associated with expression of such proteins in a fully replicating virus can be avoided by the defective character of the vector used as described herein.

Examples of useful immunomodulating proteins include cytokines, chemokines, complement components, immune system accessory and adhesion molecules and their receptors of human or non-human animal specificity. Useful examples include GM-CSF, IL-2, IL-12, OX40, OX40L (gp34), lymphotactin, CD40, and CD40L. Further useful examples include interleukins for example interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), FANTES, macrophage inflammatory peptides MIP-1a and MIP-1b, complement components and their receptors, or an accessory molecule such as B7.1. B7.2. ICAM-1, 2 or 3 and cytokine receptors. OX40 and OX40-ligand (gp34) are further useful examples of immunomodulatory proteins. Immunomodulatory proteins can for various purposes be of human or non-human animal specificity and can be represented for present purposes, as the case may be and as may be convenient, by extracellular domains and other fragments with the binding activity of the naturally occuring proteins, and muteins thereof, and their fusion proteins with other polypeptide sequences, e.g. with immunoglobulin heavy chain constant domains. Where nucleotide sequences encoding more than one immunomodulating protein are inserted, they can for example comprise more than one cytokine or a combination of cytokine(s) and accessory/adhesion molecule(s).

Immune response evoked by the use of such vectors encoding such products can include immune responses of a variety of types that can be stimulated by the virus, e.g. a response against a virally-encoded protein, and/or a response against a host antigen, being a response stimulated by the viral vector or by the expression of the heterologous gene encoded thereby. Among the uses of the mutant virus vectors as described herein is e.g. to protect a subject of a susceptible species against infection by a corresponding wild-type virus when the subject is treated therewith, e.g. infected therewith, e.g. by direct immunisation.

The genetic material encoding an immunomodulatory protein can be carried in the mutant viral genome as an expressible open reading frame encoding a hybrid or fusion protein which comprises a polypeptide region having homology to and functionality of an immunomodulatory protein, linked to a polypeptide region having another homology and optionally another functionality. For example, the immunomodulatory protein can be, comprise, or correspond in functionality to the gp34 protein identified as a binding partner to human Ox-40 (see W Godfrey et al, J Exp Med 180(2) 1994 pp 757–762, and references cited therein, including S Miura et al, Mol Cell Biol 11(3) 1991, pp 1313–1325). The version of this protein functionality that can be encoded in the mutant viral genome can correspond to the natural gp34 sequence itself, or to a fragment thereof, or to a hybrid expression product e.g. based on the (C-terminal) extracellular (binding) domain of gp34 fused to another protein, e.g. to the constant region of an immunoglobulin heavy chain such as human IgGl, e.g. with the extracellular domain of gp34 (a type 2 membrane protein) fused at its N-terminal to the C-terminal of the immunoglobulin constant domain.

Others of the immunomodulatory proteins can also be carried and expressed in such derivative and hybrid forms. It is also understood that mutations of the amino acid sequences of such immunomodulatory proteins can be incorporated. Included here are proteins having mutated sequence such that they remain homologous, e.g. in sequence, function, and antigenic character, with a protein having the corresponding parent sequence. Such mutations can preferably for example be mutations involving conservative amino acid changes, e.g. changes between aminoacids of broadly similar molecular properties. For example, interchanges within the aliphatic group alanine, valine, leucine and isoleucine can be considered as conservative. Sometimes substitution of glycine for one of these can also be considered conservative. Interchanges within the alliphatic group aspartate and glutamate can also be considered as conservative. Interchanges within the amide group asparagine and glutamine can also be considered as conservative. Interchanges within the hydroxy group serine and threonine can also be considered as conservative. Interchanges within the aromatic group phenylaalanine, tyrosine and tryptophan can also be considered as conservative. Interchanges within the basic group lysine, arginine and histidine can also be considered conservative. Interchanges within the sulphur-containing group methionine and cysteine can also be considered conservative. Sometimes substitution within the group methionine and leucine can also be considered conservative. Preferred conservative substitution groups are aspartate-glutamate; asparagine-glutamine; valine-leucine-isoleucine; alanine-valine; phenylalanine-tyrosine; and lysine-arginine. In other respects, mutated sequences can comprise insertion and/or deletions.

In certain examples the immunomodulating protein can comprise a cytokine, preferably granulocyte macrophage colony stimulating factor (GM-CSF), e.g. murine or preferably human GM-CSF.

Murine and human GM-CSFs are both known: the murine GM-CSF gene encodes a polypeptide of 141 amino acids, the mature secreted glycoprotein having a molecular weight of between 14 k–30 k daltons depending on the degree of glycosylation. GM-CSF generically is a member of the haematopoietic growth factor family and was first defined and identified by its ability to stimulate in vitro colony formation in haematopoietic progenitors. GM-CSF is a potent activator of neutrophils, eosinophils and macrophage-monocyte function, enhancing migration, phagocytosis, major histocompatibility complex (MHC) expression, and initiating a cascade of bioactive molecules which further stimulate the immune system. GM-CSF is currently being clinically evaluated for treatment of neutropenia following chemotherapy and as an adjuvant in cancer therapy.

The heterologous nucleotide sequence employed can comprise a heterologous gene, gene fragment or combination of genes provided it encodes an immunomodulating protein as defined above.

According to examples of the invention, combinations of two or more immunomodulatory proteins can be encoded for the purposes described herein within one virus vector, or a mixture of two or more vectors each containing at least one gene encoding a different immunomodulatory product can be used. In particular examples, given for illustration only and not limitation, combinations involving IL2, GMCSF, lymphotactin and/or CD40L can be used with each other or with others of the immunomodulatory proteins cited above. Each of the other binary combinations of the immunomodulatory proteins mentioned above are also given by, and within the scope of, this disclosure.

Examples of mutant virus as provided hereby can be capable of protecting a susceptible species, immunised therewith, against infection by the corresponding wild-type virus. The mutant virus can also carry a mutation which enables it to cause expression in host cells of antigen for example corresponding to another pathogen, eg. a bacterial or viral pathogen, and thereby be able to confer immunity against such another pathogen on a host of a susceptible species immunised with such a mutant virus.

Examples of such antigens are papilloma virus proteins L1 and L2, HIV proteins, gag, pol, env and nef, chlamydia antigens (such as the chlamydia Major Outer Membrane Protein MOMP) and Chlamydia heat shock proteins.

Alternatively the antigen can be a tumour associated antigen whereby the anti-tumour activity of the CTLs associated with tumour cell depletion is enhanced. It has been found that specific cytokines such as tumour necrosis factor-α, interferon gamma, interleukin-2, interleukin-4 and interleukin-7 are particularly useful in this regard. Tumour associated antigens and their role in the immunobiology of certain cancers is discussed for example by P van der Bruggen et al, Current Opinion in Immunology 4(5) (1992) 608–612. Particular examples of such antigens which are envisaged for use in the context of the present application are E6 and E7 antigens of human papillomavirus (especially for example of types 6, 11, 16, 18, etc); Epstein-Barr virus-derived proteins, e.g. those identified in references 24 and 25 in P van der Bruggen et al., cited above; antigens of the MAGE series as identified in T. Boon, Adv Cancer Res 58 (1992) pp 177–210 and/or MZ2-E and other antigens as identified in P. van der Bruggen et al, Science 254 (1991) 1643–1647; melanoma proteins, e.g. human tyrosinase; and mucins such as those identified in P. O. Livingston, in current Opinion in Immunology 4 (5) (1992) pp 624–629; e.g. MUC1 as identified in J Burchell et al, Int J. Cancer 44 (1989) pp 691–696.

In general, mutant virus can be based on a double-stranded DNA virus, eg. a herpes virus, such as herpes simplex virus. The first gene, as referred to above, can be the glycoprotein gH gene.

The defects in the first gene can comprise deletion or complete or partial inactivation. The gene can be for example inactivated by any mutations that block expression, e.g. point or promoter mutations or inactivating insertional mutations. Preferably the first gene is deleted in its entirety.

Heterologous nucleotide sequences inserted in the genome of certain examples of the mutant virus can be expressed in infected cells, e.g. at the side of inoculation, and may be expressed during latency in infected neurones. Expression of the heterologous nucleotide sequence can be regulated on two levels, by selection of a suitable promoter, and by the inherent limitations of the mutant virus itself. The heterologous sequence can be placed under the control of any of a wide variety of known viral promoters e.g. a CMV IE promoter, or under the control of a known mammalian e.g. tissue-specific promoter. Spread of the mutant virus within the host is self-limiting and therefore expression of the heterologous nucleotide sequence in such cases is restricted to the duration of intracellular expressions at the site of inoculation. A suitable promoter can be selected, inducible or constitutive, of viral or cellular origin, to enable more precise regulation of gene expression and protein concentration. The gene sequence can be native or modified to allow localisation of the protein within a specified cellular compartment.

In a preferred embodiment, the heterologous nucleotide sequence encoding an immunomodulatory protein is inserted into the genome of the mutant virus at the locus of the first gene: most preferably, it completely replaces the said first gene which is deleted in its entirety. In this way, even if any unwanted recombination event should take place, which results in the reinsertion of the first gene from a wild source into the mutant virus, it would be most likely to eliminate the inserted heterologous nucleotide sequence. This would avoid the possibility that a replication competent viral carrier for the heterologous nucleotide sequence might be produced. Such a recombination event would be extremely rare, but in this embodiment, the harmful effects of such an occurrence would be minimised.

An advantage of immunogenic examples of the invention is to provide intracellular antigen delivery which can stimulate both antibody and cell mediated immunity and the production of effective localised cytokine concentrations in the presence of antigen without inducing systemic toxicity. For example, expression of GM-CSF in an animal vaccinated with such a viral vector, in cells of the treated animal that have been infected by the vector, occurring as a result of the presence of a GM-CSF-encoding gene in the infecting virus vector, can usefully enhance the level of specific and/or neutralising antibody response by the vaccinated animal to viral or tumour antigens.

The combinations of cytokine and antigen can enhance the host response to the associated antigen. In turn this can increase the immunogenicity of poorly immunogenic proteins, and can allow a dose reduction with more effective antigens.

Examples of mutant viruses hereby provided can be used as immunogens, e.g. for prophylactic or therapeutic use in generating an immune response in a subject treated therewith. Embodiments of the invention also provides for use of a mutant virus as hereby provided in the preparation of an immunogen such as a vaccine for therapeutic or prophylactic use. A particular application is in the field of tumour therapy as discussed above, where as mentioned for example the role of the immunogen can be to stimulate immune response directed against endogenous tumour antigens.

The present invention also provides a immunogen such as a vaccine comprising a mutant virus as hereby provided, eg. an immunogenic preparation such as a vaccine comprising such mutant virus together with a pharmaceutically acceptable vehicle such as is used in the preparation of live vaccines, and can optionally include adjuvant.

The mutant virus can for example be formulated into an immunogenic or vaccine preparation in a dose containing for example up to about $5\times10^7$ pfu of the mutant virus, e.g. up to about $5\times10^6$ pfu or up to about $5\times10^5$ pfu.

The mutant viruses as hereby provided can be manufactured by a method of involving the culture of cells which have been infected with the mutant virus, the cells also expressing a gene which complements the first defective viral gene so as to allow production of infectious virus particles containing the defective genome, and recovering the mutant virus from the culture.

In immunogenic examples of the viruses disclosed herein, a second viral gene which normally functions to downregulate a host immune response against virus carrying such a second gene can be inactivated, e.g. deleted, and the resulting mutant virus used as a safe vector for delivering to the immune system of an infected host a protein such as an immunostimulatory protein or antigen normally foreign to the virus: this can be achieved by inserting, into the genome of the virus, nucleic acid sequences coding for such a protein, in such a way as to cause their expression during infection of host cells by the virus. For example, a gene encoding a desired foreign antigen can be inserted in an effective manner by cloning the desired gene text to a viral promoter, to obtain a DNA cassette containing the gene and the promoter; cloning the cassette into a suitable plasmid;

and co-transfecting the plasmid into a complementing cell line along with DNA purified from the mutant virus with its defect in a gene of which the product is provided by the cell line; and screening of recombinant virus. An example of the application of somewhat analogous technique is described, for example, in respect of a gene encoding SIV gp120 antigen, in WO92/05263 (Immunology Ltd: Inglis et al).

Such examples of genetically disabled virus vectors can be used in processes of providing an immunostimulus to a treated human or non-human animal subject, e.g. for purposes of cancer immunotherapy. The use of the vectors can be either direct, e.g. by administration to the subject, e.g. into the site of a solid tumour, or it can be indirect. For example the use of the vector can comprise:

(i) contacting a defective virus vector ex-vivo with a preparation of cells capable after infection with the vector of providing an immunostimulus to a subject to be treated; and (ii) using the infected cells to deliver an immune stimulus to the subject to be treated, e.g.

(a) by direct administration of the infected cells as a vaccine e.g. after inactivation before administration, e.g. after irradiation, or (b) by indirect use of the cells to prime or stimulate ex-vivo immune-competent cells such as cells of the immune system of the subject to be treated, followed by re-administration of the immune-competent cells e.g. without concurrent administration of virus or virus-infected cells. Any cells unwanted in this connection can for example be removed by a purification process comprising negative depletion, e.g. by selective removal of cells of unwanted type e.g. with corresponding antibodies or other binding agents.

Cells infected ex-vivo with the virus vector can be either autologous cells or heterologous cells, e.g. heterologous cells obtained from one or a plurality of subjects with a condition similar to that which is to be treated. The cells can be of a single cell type or of a mixture of cell types, e.g. they can comprise cells of one or plural cell lines established from clinical tumour samples. Thus, for example, in the case where an immune stimulus is to be given, directed against melanoma cells, the heterologous cells can be melanoma cells from one or more subjects with melanoma, other than the subject to be treated, or including the subject to be treated. Corresponding arrangements can be made for other specificities of immune stimulus.

The infected cells for administration to provide an immune stimulus can preferably be inactivated, e.g. by irradiation, before administration. They can preferably be incubated for a sufficient time before inactivation to allow them to express the heterologous gene carried by the viral vector.

According to examples of the invention there is also provided a does or calibrated preparation of vector-infected, optionally inactivated cells, for administration to a subject to be treated to an immune stimulus, which has been dosage-calibrated, e.g. by reference to the number of concentration of infected cells it contains, or by reference to the quantity of heterologous gene product it expresses.

Alternatively the genetically disabled virus vectors can be used in in-vivo administration of a quantity or concentration of the virus vector to contact and thereby tumour cells in vivo, e.g. cells of a solid tumour such as for example a melanoma.

Among the cells that can usefully be treated in this way are for example malignant cells of human and non-human animals, especially for example malignant cells related to blood cells, e.g. leukaemic cells, e.g. CD34+ cells (haematopoietic cells) see example, cell types as mentioned in R Jurecic et al, ch 2, pp 7–30 in 'Somatic Gene Therapy' CRC Press 1995, ed. P. L. Chang).

Immunological treatment of tumours using cytokines is reviewed by H Tahara et al., ch.15, pp 263–285 in 'Somatic Gene Therapy' CRC Press 1995, ed. P. L. Chang). The vectors described herein can be applied to the immunological applications of the cytokines and methods of treatment reviewed in the cited review by H Tahara et al, using appropriate adaptations and modifications as will be readily apparent to thos skilled in the field.

The invention also finds further application in vitro for example in in vitro treatments such as expansion of T cells such as virus-specific cytotoxic T cells. Two complications of many immunosuppressive or cytotoxic treatments are generalised viraemia following virus infections and expansion of virus-transformed cells as a result of latent virus reactivation. This is due to the fact that the normal mechanism for controlling such infections is impaired as a result of the treatment. One possible solution of this problem is to produce in vitro the appropriate cytotoxic T cells which are capable of controlling the virus infected cells. This can be done by isolating peripheral blood mononuclear cells or lymphocytes or T cells prior to treatment of the patient and stimulating such cells in vitro with a preparation of live virus. It is necessary to use live virus as cytotoxic T cells are generally directed against peptides derived from foreign proteins which are synthesised within the antigen-presenting cell: inactivated virus or individual proteins are very poor at raising cytotoxic T cell responses. The activated cells are then expanded in culture over a period of weeks with further re-stimulated with antigen and a growth factor such as interleukin-2. However, there is the concern that there might be residual live virus in the cell culture when the CTLs are re-infused into the patient. Use of a disabled virus capable of inducing CTL activity but incapable of spread within the patient, if inadvertently given along with the in vitro expanded cells, can therefore provide an advantage over a system that uses replication competent virus.

Hence the invention further provides a method for producing virus-specific cytotoxic T cells which method comprising;

(a) isolating a sample of blood mononuclear cells, lymphocytes or T cells from a patient;

(b) culturing said sample in vitro in the presence of a mutant virus which is defective in respect of a first gene essential for the production of infectious virus, and which can optionally include a heterologous nucleotide sequence which encodes an immunomodulating protein; and (c) reinfusing cultured cells into the patient.

Certain vectors provided by the present invention can also be applied to gene therapy, e.g. corrective gene therapy. In such an application the vector can further encode a gene to be delivered by way of corrective gene therapy, e.g. a gene encoding ADA or another gene to be administered for such a purpose e.g. as mentioned above. A vector as described herein encoding the immunomodulatory protein TGF beta can be particularly suitable as a vector for corrective gene therapy, to downregulate the response of the treated subject, who will usually be treated either directly with a vector provided hereby or with live cells, autologous or heterologous, after their infection with the vector. Negative immunomodulatory effects can be provided by this or other suitable choice of immunomodulatory proteins. Further choice of immunomodulatory proteins for this application can for example be as follows: Inhibition of Th1 effects can be achieved with vectors encoding Th2 cytokines or vice versa: for example a vector encoding IL10 against Th1 effects and a vector encoding IFN-gamma against Th2 effects. Immune response can be further downregulated by using a vector that encodes for example an immune downregulatory gene of viral or other pathogenic origin, e.g. a vector encoding a herpes ICP47 gene (from HSV1 or HSV2) or additionally encoding another known immune-downregulatory gene, e.g. E3-gp19k of adenovirus (see G Fejer et al, J Virol 68 (1994) 4871–81)). Literature procedures of gene therapy, e.g. U.S. Pat. No. 5,399,346 (W F Anderson et al), can be adapted with the use of the vectors provided hereby.

Alternatively the systems disclosed herein can be used to express immunomodulating proteins, particularly authentic mammalian proteins. Many expression systems are available for the manufacture of clinically relevant proteins. The expression system selected and in particularly the organism used will have a profound influence on the final character of the protein, with probable influences on molecular weight and degree of glycosylation, immunogenicity, toxicity and potency. GM-CSF has been successfully manufactured in *E.coli* (Libby, R. T. et al DNA 1987 Jun 6), yeast (Price, V et al Gene 1987 55 (2–3)) and mammalian cell culture systems, however considerable differences are seen in yield, product potency and therefore cost, toxicity and in vivo clearance rates (Dorr, R. T. Clin Ther. 1993 Jan.Feb 15, D Hovgaard Eur J. Hematology 1993 Jan 50) These parameters in turn can affect the economic and technical viability of treating a particular disease with a protein product.

In a further aspect the invention provides a method of producing an immunomodulating protein, which method comprises culturing in-vitro a cell line infected with a mutant virus which is defective in respect of a first gene essential for the production of infectious virus, and which includes a heterologous nucleotide sequence which encodes an immunomodulating protein, said cell line being a complementary cell line capable of supporting replication of said mutant virus, and optionally thereafter isolating immunomodulating protein from said culture.

In particular, recombinant HSV vectors have the potential to be used as alternative expression system where an authentic mammalian cell derived product is required and where conventional stable cell expression systems are unsuccessful or inappropriate. The system can operate as a conventional batch culture system where complementing cells i.e. CR1 cells (designation of a recombinant complementing Vero-derived cell line expressing gH of HSV1) are grown to confluence using standard tissue culture systems, the cells are infected at high titre with the recombinant virus containing the coding sequence for heterologous gene expression. At an appropriate time following infection the culture supernatants can be harvested and processed to recover the relevant protein.

In order to illustrate the present invention more fully, embodiments will be described by way of example only and not by way of limitation. The construction and properties of a gH-defective virus is described in Forrester et al, 1992 J. Virol. 66, p 341, in WO92/05263 and in WO94/21807. Further, all genetic manipulation procedures can be carried out according to standard methods as described in "Molecular Cloning" A laboratory Manual, eds. Sambrook, Fritsch and Maniatis, Cold Spring Harbor Laboratory Press 1989.

The examples are illustrated non-limitatively by reference to the accompanying drawings, in which FIGS. 1 to 6 are diagrams illustrating the construction of plasmids, pIMMB45, pIMMB56, pIMMB46, pIMC14, pIMR1 and pIMR3, respectively. FIG. 7 is a recombination diagram illustrating the introductory description of the invention.

The description below particularly includes:

Construction of gH-deleted HSV1 and HSV2 encoding (murine) GM-CSF at the site of deletion of the gH gene and able to cause expression of the GM-CSF in an infected cell:

Testing the effect of such a vector as in immunogen (vaccine):

Construction of gH-deleted HSV2 encoding human GM-CSF at the site of deletion of the gH gene and able to cause expression of the GM-CSF in an infected cell: and Construction of gH-deleted HV2 encoding human IL-2 at the site of deletion of the gH gene and able to cause expression of the IL-2 in an infected cell.

Construction of gH-deleted HSV1 and gH-deleted HSV2 expressing GH-CSF

The gH-deleted HSV1 virus and gH-deleted HSV2 virus was propagated in the complementing cell lines. These cell lines have been engineered to express the HSV-1 gH gene or the HSV-2 gH gene respectively. Such cell lines can be constructed as described in WO94/05207 and WO94/21807 and references cited therein. The following section provides a further description of the construction of suitable cell lines, and starts with the construction of certain plasmids.

Source of virus DNA:

Where HSV viral DNA is required, it can be made for example (in the case of HSV2) from the strain HG52 by the method of Walboomers and Ter Schegget (1976) Virology 74, 256–258, or by suitable adaptations of that method. An elite stock of the HG52 strain is kept at the Institute of Virology, MRC Virology Unit, Church Street, Glasgow, Scotland, UK. The DNA of other HSV-2 strains is likely to be very similar in this region, and strains G and MS for example can be obtained from the ATCC, Rockville, Md., USA.

Construction of plasmid pIMC05

A 4.3 kb Sst-1 fragment encoding the HSV-1 (HFEM) gH gene and upstream HSV-1 gD promoter (−392 to +11) was excised from the plasmid pgDBrgH (Forrester et al., op. cit.), and cloned into pUC119 (Vieira & Messing, 1987) to produce plasmid pUC119gH. A not 1 site was introduced into plasmid pUC119gH by site-directed mutagenesis, 87 bp downstream of the gH stop codon. The resulting plasmid, pIMC03, was used to generate a Not 1-Sst 1 fragment which was repaired and ligated into the eucaryotic expression vector pRc/CMV (Invitrogen Corporation), pre-digested with Not 1 and Nru 1 to remove the CMV IE promoter. The resulting plasmid, pIMC05, contains the HSV-1 gH gene under the transcriptional control of the virus inducible gD promoter and BGH (Bovine Growth Hormone) poly A. It also contains the neomycin resistance gene for selection of G418 resistant stable cell lines.

Construction of gH-deleted HSV-1 complementing cell line

The plasmid pIMC05 was transfected into Vero (ATCC no. 88020401) cells using the $CaPO_4$ technique (Sambrook, Fritsch & Maniatis, A Laboratory Manual, Cold Spring Harbor laboratory Press). Cells were selected by dilution cloning in the presence of G418 and a clonal cell line was isolated. Following expansion and freezing, cells were seeded into 24 well plates and tested for their ability to support the growth of gH-negative virus, by infection with SC16ΔgH (Forrester et al, op. cit) at 0.1 pfu/cell. Virus plaques were observed 3 days post infection confirming expression of the gH gene.

Construction of BHK TK—cell line These cells were produced by transfection of plasmid pIMC05 into thymidine kinase negative (TK–) BHK cells (ECACC No. 85011423) in the same manner as that described for gH-deleted HSV-1 and gH-deleted HSV-2 complementary cells.

Construction of plasmid PIMC08

Plasmid pIMMB24 containing the HSV-2 gH gene is constructed from two adjacent BamHI fragments of HSV-2 strain 25766. The plasmids are designated pTW49, containing the approximately 3484 base pair BamHI R fragment, and pTW54, containing the approximately 3311 base pair BamHI S fragment, both cloned into the BamHI site of pBR322. Equivalent plasmids can be cloned easily from many available strains or clinical isolates of HSV-2. The 4' end of the HSV-2 gene is excised from pTW54 using BamHI and KpnI, to produce a 2620 base pair fragment which is gel-purified. The 3' end of the HSV-2 gH gene is excised from pTW49 using BamHI and SalI, to produce a 870 base pair fragment which is also gel-purified. The two fragments are cloned into pUC119 which had been digested with SalHI and KpnI. This plasmid now contains the entire HSV-2 gH gene.

Plasmid pIMC08 containing the HSV-2 (strain 25766) gH gene was constructed as follows. Plasmid pIMM824 was digested with NcoI and BstXI and the fragment containing the central portion of the gH gene was purified from an agarose gel. The 5' end of the gene was reconstructed from two oligonucleotides CE39 and CE40 which form a linking sequence bounded by HindIII and NcoI sites.

The 3' end of the gene was reconstructed from two oligonucleotides CE37 and CE38 which form a linking sequence bounded by BstXI and NotI sites.

CE39 5' AGCTTAGTACTGACGAC 3' (SEQ ID NO:1)

CE40 5' CATGGTCGTCAGTACTA 3' (SEQ ID NO:2)

CE37 5' GTGGAGACTCGAATAATCGCGAGC 3' (SEQ ID NO:3)

CE38 5' GGCCGCTCGCGATTATTCGCGTCTCCA-CAAAA 3' (SEQ ID NO:4)

The two oligonucleotide linkers and the purified NcoI-BstXI gH fragment were cloned in a triple ligation into HindIII-NotI digested pIMC05, thus replacing the HSV-1gH gene by the HSV-2 gH gene. The resultant plasmid was designated pIMC08.

Construction of gH-deleted HSV-2 complementary cell line

The plasmid pIMC08, contains the HSV-2gH gene under the transcriptional control of the virus inducible gD promoter and BGH (Bovine Growth Hormone) poly A. It also contains the neomycin resistance gene for selection of G418 resistant stable cell lines. The plasmid pIMC08 was transfected into Vero (ATCC no. 88020401) cells using the CaPO4 technique (Sambrook, Fritsch & Maniatis, A Laboratory Manual, Cold Spring Harbor Laboratory Press). Cells were selected by dilution cloning in the presence of G418 and a clonal cell line was isolated. Following expansion and freezing, these cells, designated CR2 cells, were seeded into 24 well plates, and infected with the gH deleted HSV-1 9SC16 gH) at 0.1 pfu/cell. Virus plaques were observed 3 days post infection confirming expression of the gH gene.

Construction of recombination plasmids a) pIMMB56+ pIMMB56+ is a vector with a lacZ cassette flanked by HSV-2 sequences from either side of the gH gene. It is made as follows; the two PCR fragments made by oligos MB97-MB96 and by oligos MB57–MB58 are digested with the restriction enzymes appropriate to the sites that have been included in the PCR oligonucleotides. The MB97-MB96 fragment is digested with HindIII and HpaI. The MB57–MB58 fragment is digested with HpaI and EcoRI. These fragments are then ligated into the vector pUC119 which has been digested with HindIII and EcoRI. The resultant plasmid is called pIMMB45 (FIG. 1).

The oligonucleotides used for PCR are shown below:

```
                                            (SEQ ID NO:5)
            HindIII
MB91:   5'  TCGAAGCTTCAGGGAGTGGCGCAGC 3'
              HpaI (SEQ ID NO:6)
MB96:   5'  TCAGTTAACGGACAGCATGGCCAGGTCAAG 3'
      HpaI (SEQ ID NO:7)
MB57:   5'  TCAGTTAACGCCTCTGTTCCTTTCCCTTC 3'
      EcoRI (SEQ ID NO:8)
MB58:   5'  TCAGAATTCGAGCAGCTCCTCATGTTCGAC 3'
```

To allow for easy detection of the first stage recombinants, the *E.coli* beta-galactosidase gene, under the control of an SV40 promoter is inserted into pIMMB45. The SV40 promoter plus beta-galactosidase gene is excised from the plasmid pCH110 (Pharmacia) using BamHI and Tth III 1. The ends are filled in using the Klenow fragment of DNA polymerase. The fragment is gel-purified. The plasmid pIMMB45 is digested with HpaI, phosphatased with Calf Intestinal Alkaline Phosphatase (CIAP) to abolish self ligation, and gel-purified. The gel-purified fragments are then ligated together to produce the plasmid pIMMB56+ (see FIG. 2).

b) pIMMB46 pIMMB46 contains sequences flanking the HSV-2 gene, with a central unique HpaI site. Any gene cloned into this site can be inserted by recombination into the HSV-2 genome at the gH locus. If the virus is a TK-negative gH-negative virus, (for example made using the pIMMB56+ plasmid described above) then the plasmid will replace the 3' end of the TK gene, thus restoring TK activity and allowing selection for TK-positive virus.

The two PCR fragments made by oligos MB94–MB109 and by oligos MB-57–MB108 are digested with the restriction enzymes appropriate to the sites that have been included in the PCR oligonucleotides. The MB94–MB109 fragment is digested with HindIII and HpaI. The MB57–MB108 fragment is digested with HpaI and EcoRI. These fragments are then ligated into the vector pUC119 which has been digested with HindIII and EcoRI. The resultant plasmid is called pIMMB846 (see FIG. 3). The oligonucleotides used are as follows:

```
                                            (SEQ ID NO:9)
            HpaI
MB57:   5'  TCAGTTAACGCCTCTGTTCCTTTCCCTTC 3'
      EcoRI (SEQ ID NO:10)
MB108:  5'  TCAGAATTCGTTCCGGGAGCAGGCGTGGA 3'
      HindIII (SEQ ID NO:11)
MB94:   5'  TCAAAGCTTATGGCTTCTCACGCCGGCCAA 3'
      HpaI (SEQ ID NO:12)
MB109:  5'  TCAGTTAACTGCACTAGTTTTAATTAATACGTATG 3'
``` c) pIMC14

The plasmid pRc/CMV (Invitrogen Corporation) was digested with the restriction enzymes NruI, PvuII and BsmI and a 1066 base pair NruI-PvuII fragment was isolated from an agarose gel. The fragment was cloned into HpaI digested pIMMB46 (see FIG. 4). The resultant is named pIMC14.

The pRc/CMV fragment contains the cytomegalovirus major immediate early promoter (CMV-IE promoter) and the bovine growth hormone (BGH) poly A addition site. This plasmid, pIMC14, is a general recombinant plasmid with unique sites for the insertion of foreign genes which can then be recombined into an HSV-2 gH-deleted DISC vector.

d) pIMR1

The plasmid pIMR1 is a recombination vector for the insertion of the murine GM-CSF gene, under the control of the CMV-IE promoter, into a DISC HSV-2 vector. pIMC14 is digested with XbaI, phosphatased with CIAP, gel purified and the overhanging ends made flush with Klenow polymerase. The murine GM-CSF gene is excised from the plasmid pGM 3.2FF (referred to as pGM3.2 in Gough et al. EMBO Journal 4, 645–653, 1985) (or from the equivalent plasmid constructed as described below), by a two stage procedure. Firstly pGM 3.2FF is digested with EcoRI and a 1048 base pair fragment is gel-purified. This fragment is then digested with HinfI and StuI. The 495 base pair fragment is gel-purified and the ends repaired with Klenow polymerase. This fragment is then cloned into multi cloning site of pIMC14, prepared as described above. The resulting plasmid is designated pIMR1 (see FIG. 5).

An alternative plasmid equivalent to pGM3.2, can be constructed as follows.

A library of cDNA clones is constructed from a cloned T-lymphocyte line (from a BALB/c strain of mouse), such as LB3 (Kelso et al, J Immunol. 132, 2932, 1984) in which the synthesis of GM-CSF is inducible by concanavalin A. The library is searched by colony hybridisation with a sequence specific to the murine GM-CSF gene (see Gough et al, EMBO J, 4, 645, 1985 for sequence). A example of an oligonucleotide usable in this case is 5' TGGATGACAT GCCTGTCACA TTGAATGAAG AGGTAGAAGT 3' (SEQ ID NO:13). Clones of over 1 kb are picked and sequenced to check that they are GM-CSF. These operations can be carried out as described in "Molecular Cloning: A Laboratory Manual", ed. Sambrook, Fritsch and Maniatis, Cold Spring Harbor Laboratory Press. Such an operation results in a clone containing the complete GM-CSF sequence which can be excised with HinfI and StuI as described for pGM3.2.

e) pIMR3

In the plasmid pIMR1 the open reading frame for the GM-CSF gene is preceded by a short open reading frame (ORF) of 15 base pairs. Because it was thought possible that this might interfere with the expression of GM-CSF, the plasmid pIMR1 is altered so that this small reading frame was removed. pIMR1 was digested with NotI and PpuMI. The digested vector was phosphatased with calf intestinal alkaline phosphatase (CIAP) and gel-purified. The sequences between the two restriction enzyme sites were replaced by a short piece of double-stranded DNA generated by the annealing of two oligonucleotides CE55 and CE56:

CE55    GGCCGCTCGAACATGGCCCAC-
    GAGAGAAAGGCTAAG (SEQ ID NO:14)

CD56 GACCTTAGCCTTTCTCTCGTGGGCCAT-
    GTTCGAGC (SEQ ID NO:15)

The oligonucleotides are constructed so as to have overhanging ends compatible with the NotI and PpuMI ends generated by the digestion of pIMR1. The two oligonucleotides are annealed, phosphorylated, and ligated to the NotI-PpuMI-digested pIMR1. The resultant vector was designated pIMR3. The sequences in the relevant region are shown below:

```
pIMR1
TTAATACGAC TCACTATAGG GAGACCGGAA GCTTGGTACC GAGCTCGGAT        (SEQ ID NO:16)

CCACTAGTAA CGGCCCCCAG TGTGCTGGAA TTCTGCAGAT ATCCATCACA

CTGGCGGCCG CTCGAGCATG CATCTAGCCT TTTGACTACA ATGCCCACGAGA    NotI
      Short ORF                        Start of GM-CSF

GAAAGGCTAAGGTCCTG

PpuMI
pIMR3
TTAATACGAC TCACTATAGG GAGACCGGAA GCTTGGTACC GAGCTCGGAT        (SEQ ID NO:17)

CCACTAGTAA CGGCCGCCAG TGTGCTGGAA TTCTGCAGAT ATCCATCACA

CTGGCGGCCG CTCGAACATG GCCCACGAGA GAAAGGCTAA GGTCCTG
    Not I         Start                            PpuMI
```

To make an HSV-1 DISC virus expressing the GM-CSF protein, a different set of plasmids is made:

f) pIMMB34

This is a recombination vector containing sequences flanking the HSV-1 gH gene. The left side flanking sequences inactivate TK gene which lies adjacent to the gH gene. The two PCR fragments made by oligos MB97–MB100 and by oligos MB61-MB58 are digested with the restriction enzymes appropriate to the sites that have been included in the PCR oligonucleotides. The MB97–MB100 fragment is digested with HindIII and HpaI. The MB61-MB58 fragment is digested with HpaI and EcoRI. These fragments are then ligated into the vector pUC119 which has been digested with HindIII and EcoRI. The resultant plasmid is called pIMMB34. The oligonucleotides used are as follows:

```
                                                  (SEQ ID NO:18)
            HindIII
MB97:   5'  TCGAAGCTTCAGGGAGTGGCGCAGC 3'

(SEQ ID NO:19)
            HpaI
MB100   5'  TCAGTTAACGGCCAGCATAGCCAGGTCAAG 3'

(SEQ ID NO:20)
```

-continued

```
       HpaI
MB61:   5'    TCAGTTAACAGCCCCTCTTTGCTTTCCCTC 3'
                                              (SEQ ID NO:21)
       EcoRI
MB58:   5'    TCAGAATTCGAGCAGCTCCTCATGTTCGAC 3'
``` g) pIMMB55+

To allow for easy detection of the first stage recombinants, the *E.coli* beta-galactosidase gene, under the control of an SV40 promoter is inserted into pIMMB34. The SV40 promoter plus beta-galactosidase gene is excised from the plasmid pCH110 (Pharmacia) using BamHI and Tth III 1. The ends are filled in using the Klenow fragment of DNA polymerase. The fragment is gel-purified. The plasmid pIMMB34 is digested with HpaI, phosphatased with Calf Intestinal Alkaline Phosphatase (CIAP) to abolish self ligation, and gel-purified. The gel-purified fragments are then ligated together to produce the plasmid pIMMB55+.

h) pIMMB63:

pIMMB63 is made from HSV-1 strain KOS (m) DNA. pIMMB63 contains sequences flanking the HSV-1 gH gene, with a central unique HpaI site. Any gene cloned into this site can be inserted by recombination into the HSV-1 genome at the gH locus. If the virus is a TK-negative virus (for example made using the pIMMB55+ plasmid described above) then the plasmid will replace the 3' end of the TK gene, thus restoring TK activity and allowing selection for TK-positive virus.

The two PCR fragments made by oligos MB98-MB63 and by oligos MB61-MB58 are digested with the restriction enzymes appropriate to the sites that have been included in the PCR oligonucleotides. The MB98-MB63 fragment is digested with HindIII and HpaI. The MB61-MB58 fragment is digested with HpaI and EcoRI. These fragments are then ligated into the vector pUC119 which has been digested with HindIII and EcoRI. The resultant plasmid is called pIMMB63. The oligonucleotides used are as follows:

```
                                              (SEQ ID NO:22)
       HindIII
MB98:   5'    TCAAAGCTTATGGCTTCGTACCCCTGCCAT 3'

(SEQ ID NO:23)
       HpaI
MB63:   5'    TCAGTTAACGGACCCCGTCCCTAACCCACG 3'

(SEQ ID NO:24)
       HpaI
MB61:   5'    TCAGTTAACAGCCCCTCTTTGCTTTCCCTC 3'

(SEQ ID NO:25)
       EcoRI
MB58:   5'    TCAGAATTCGAGCAGCTCCTCATGTTCGAC 3'
``` i) pIMX1.0

This plasmid is a general recombination plasmid with unique sits for the insertion of foreign genes which can then be recombined into an HSV-1 gH-deleted DISC vector. The plasmid pRc/CMV was digested with NruI and PvuII and a 1066 bp fragment, which contains CMV IE promoter and a polyA signal, was blunt ended with Klenow polymerase and inserted into the unique HpaI site of plasmid pIMMB63. This plasmid is names pIMX1.0. The multiple cloning site contained between the CMV IE promoter and the polyA signal is ideal for cloning other genes into the plasmid and their subsequent introduction into DISC HSV-1.

j) pIMX3.0

The plasmid pIMX3.0 is a recombination vector for the insertion of murine GM-CSF, under the control of CMV IE promoter, into the deleted gH region of type I DISC HSV. This plasmid was constructed by inserting the murine GM-CSF which was excised out from plasmid pGM3.2FF (op. cit.) with SmaI and DraI, into the unique BsaBI site of pIMX1.0. This plasmid, pIMX3.0, is the HSV-1 equivalent of pIMR3.

Construction of recombinant virus

Recombinant virus expressing GM-CSF was made in two stages. In the first stage the gH gene, and part of the TK gene are replaced by a "lacZ cassette", consisting of the SV40 promoter driving the *E.coli* lacZ gene. This virus has a TK minus phenotype and also gives glue plaques when grown under an overlay containing the colourigenic substrate X-gal. This recombinant virus can now be conveniently used for the insertion of foreign genes at the gH locus. Genes are inserted in conjunction with the missing part of the TK gene. At the same time the lacZ cassette is removed. These viruses can be selected on the basis of a TK-positive phenotype, and a white colour under X-gal.

a) Construction of first stage recombinant with VS40-lacZ cassette replacing gH.

Recombinant virus was constructed by transfection of viral DNA with the plasmid pIMMB56+ (for HSV-2) or pIMMB55+ (for HSV-1). viral DNA is purified on a sodium iodide gradient as described in Walboomers & Ter Schegget (1976) Virology 74, 256–258.

Recombination is carried out as follows:

a) First stage

A transfection mix is prepared by mixing 5 $\mu$g of viral DNA, 0.5 $\mu$g of linearised plasmid DNA (linearised by digestion with the restriction enzyme ScaI) in 1 ml of HEBS buffer (137 mM NaCl, 5 mM KCl, 0.7 mM Na2HPO$_4$, 5.5 mM glucose, 20 mM Hepes, pH 7.05). 70 $\mu$l of 2M CaCl$_2$ is added dropwise, and mixed gently. The medium is removed from a sub-confluent 5 cm dish of CR1 or CR2 cells and 500 $\mu$l of the transfection mix is added to each of two dishes. The cells are incubated at 37° C. for 40 minutes, when 4 ml of growth medium containing 5% foetal calf serum (FCS) are added. 4 hours after adding the transfection mix, the medium is removed and the cells washed with serum-free medium. The cells are then 'shocked' with 500 $\mu$l per dish of 15% glycerol for 2 minutes. The glycerol is removed, the cells washed twice with serum-free medium and growth medium containing 5% FCS is added.

After 4–7 days, when a full viral cytopathic effect (CPE) is observed, the cells are scraped into the medium, spun down at 2500 rpm for 5 minutes at 4° C., and resuspended in 120 $\mu$l of Eagles minimal essential medium (EMEM). This is now a crude virus stock containing wild-type and recombinant virus. The stock is frozen, thawed and sonicated and screened for recombinants on CR1 cells at a range of dilutions. The medium contains 10 $\mu$g/ml of acyclovir, to select for TK-minus virus. After addition of the virus dilutions, the cells are overlaid with medium containing 1% low-gelling temperature agarose. After the appearance of viral plaques at about 3 days, a second overlay of agarose containing 330 $\mu$g/ml of Xgal as well as 10 $\mu$g/ml acyclovir, is added. Blue plaques are picked, within 48 hours, and transferred to 24-well dishes (1 cm2 per well) containing CR1 cells. The plaques are allowed to grow to full CPE and harvested by scraping into the medium. Multiple rounds of plaque-purification are carried out until a pure stock of virus is obtained.

The structure of the first stage recombinant is confirmed as follows. Sodium iodide purified viral DNA is prepared as before, and digested with BamHI. This digest is separated on an agarose gel and transferred to a nylon membrane. This is probed with a radiolabelled DNA fragment homologous to the sequences either side of the gH gene.

b) Second stage.

Recombination is carried out as before using viral DNA from the first stage recombinant, and the plasmid pIMR3 (for HSV-2) or pIMX3.0 (for HSV-1). After the initial harvest of virus, TK-positive recombinant viruses are selected by growth on BHK gH-positive TK-negative cells, in the presence of 0.6 μM methotrexate, 15 μM Thymidine, 9.5 μM Glycine, 4.75 μM Adenosine and 4.75 μM Guanosine. Three rounds of this selection are carried out in 6-well dishes (10 cm² per well). At each stage the infected cells are harvested by scraping into the medium, spinning down and resuspending in 200 μl of EMEM. After sonication, 50 μl of his is added to fresh BHK gH-positive TK-negative cells, and the selection continued.

After the final selection the virus infected cells are harvested as before and screened on gH-deleted HSV1 complementary cells. Overlays are added as before and white plaques are selected in the presence of Xgal. Plaques are picked as before and plaque-purified three times on said gH-deleted HSV1complementary cells.

The structure of the viral DNA is analysed as before.

Testing of vaccine potential of gH-deleted GM-CSF expressing mutant virus

The gH-deleted GM-CSF expressing mutant virus can be tested for its efficacy as a vaccine by using a mouse model system as described in Farrell et al, J. Virol. 68, 927–32, 1994. Groups of mice are vaccinated by scarification of the ear pinna with varying doses ranging from $10^2$ to $10^6$ plaque forming units (pfu) of gH-deleted mutant virus, GM-CSF expressing virus, the gH-deleted GM-CSF-expressing mutant virus, and the gH revertant. A control group is vaccinated with PBS. After 3 weeks, mice are challenged in the opposite ear pinna with $10^6$ pfu of wild-type HSV-1 (strain SC16). Five days post challenge the mice are killed the challenged ears removed and frozen at −70° C. The ears are homogenised and the amount of infectious challenge virus in each ear is determined by plaque titration. The reduction in virus titres in the vaccinated groups of mice compared to the PBS-treated controls is a measure of the protection afforded by the virus vaccine. It is known that the gH-deleted virus can completely abolish the presence of infectious virus at a vaccinating dose of 5×10^5 pfu, whilst even at 5×10^4 pfu a reduction of 1000-fold is observed. That the gH-deleted GM-CSF expressing mutant can give increased level of protection can be tested by observing complete protection from any infectious virus at lower challenge doses than in the gH-deleted mutant-virus vaccinate mice, and a greater reduction of infectious virus titres as compared to the PBS-vaccinated controls. The gH-deleted GM-CSF-carrying virus can give an increased level of antibody response as compared with a gH-deleted virus not carrying the Gm-CSF gene.

GM-CSF assay

Cos 1 cells (ECACC No. 88031701) are transfected with plasmid DNA using DEAE dextran as described in Gene Transfer and Expression, A laboratory Manual, Michael Kriegler. Supernatants from transfected Cos 1 cells or infected CR2 cells are screened for GM-CSF activity by bioassay. An IL-3/GM-CSF responsive murine hemopoietic cell line designated C2GM was obtained from Dr. E. Spooncer, Paterson Institute for Cancer Research, Christie Hospital, UK. The cell line C2GM is maintained in Fischers media with 20% horse serum, 1% glutamine and 10% conditioned cell media. The conditioned cell media is obtained from exponentially growing cultures of Wehi 3b cells (ECACC No. 86013003) which secrete murine IL-3into the media. Wehi 3b cells are maintained in RPMI 1640 media, 10% FCS and 1% glutamine.

The above examples concern the creation of HSV-1 and HSV-2 mutants which are gH-negative and which express GM-CSF.

The above description can readily be adapted to the construction of vectors expressing various immunomodulatory proteins, for example as follows:

Construction of gH-deleted HSV2 vectors expressing human GM-CSF:

Human GMCSF and its gene are described in M Cantrell et al, PNAS 82 (1985) 6250–6254; F Lee et al, PNAS 82 (1985) 3460–4364; G Wong et al, Science (1985) 228: 810–815.

DNA for cloning is obtainable by the use of PCR and oligonucleotides in standard manner, and an engineered version of the gene is also commercially available from R&D Systems Europe Ltd, Abingdon, OX14 3YS UK.

The gene can e prepared for cloning by engineering the DNA ends to ensure that a natural leader sequence and start signal for expression in a mammalian system is present at the 5' end, and, for present purposes, by adding complementary ends to match (at the 5' end) a HindIII site and (at the 3' end) a EcoRI site.

The prepared gene can then be ligated into a cloning vector pcDNA3 (Invitrogen Corporation) between the HindIII and EcoRI sites, and cloned The resulting vector is designated pcDNA3-hGMSCF. This can be digested with EcoRI, and then with HindIII, blunt-ended, and cloned into vector pIMC14 as described above, (in place of the murine gene as used in the example described above).

The resulting cloning vector with hGMCSF can then be used in adaptations of the remaining procedures already described herein, for example to make a gH-deleted defective HSV2 virus vector encoding human GMCSF at the site of deletion of the gH gene.

Construction of gH-deleted HSV2 vectors expressing human IL-2:

Human IL-2 and its gene are describe din T Taniguchi et al, Nature 302 (1983) (5906) 305–310, and in EMBL sequence HSIL02 (mRNA encoding IL2); se also R Devos et al, Nucl Acids Res 11(13) (1983) 4037–4323 (referring to bacterial expression).

DNA for cloning is obtainable e.g. from T cells, by the use of PCR and oligonucleotides in standard manner, and an engineered version of the gene is also commercially available from R&D Systems Europe Ltd, Abingdon, OX14 3YS UK.

The gene can be prepared for cloning by engineering the DNA ends to ensure that a natural leader sequence and start signal for expression in a mammalian system is present at the 5' end, and, for present purposes, by adding complementary ends to match ( at the 5' end) a HindIII site and (at the 3' end) a EcoRI site.

The prepared gene can then be ligated into a cloning vector pcDNA3 (Invitrogen Corporation) between the HindIII and EcoRI sites, and cloned. The resulting vector is designated pcDNA3-hIL02. This can be digested with EcoRI, and then with HindIII, blunt-ended, and cloned into vector pIMC14 as described above, (in place of the murine GMCSF gene as sued in the example already described).

The resulting cloning vector with human IL-2can then be used in adaptations of the remaining procedures already described herein, for example to make a gH-deleted defective HSV2 virus vector encoding human IL-2 at the site of deletion of the gH gene.

The techniques can be readily adapted to other interleukins, cytokines, chemokines, for example IL-12, lymphotactin, and CD40L, among many others.

Thus, using for example the viral vectors particularly described herein, a patient can be immunised for prophylactic or therapeutic purposes such as those mentioned herein by the administration of an immunogen or vaccine comprising a mutant virus which has a genome defective in respect of a selected gene essential for the production of infectious virus such that the virus can infect normal cells and undergo replication and expression of viral antigen genes in those cells but cannot produce normal infectious virus, the genome also having a heterologous nucleotide sequence which functions to express an immunomodulating protein, preferably encoded at the locus of the defective essential gene.

The skilled person can readily adapt this teaching to the preparation of other mutant viruses which are defective in respect of a first gene essential for the production of infectious virus, such that the virus can infect normal cells and undergo replication and expression of viral antigen in these cells but cannot produce named infectious virus and which also express a heterologous nucleotide sequence which encodes an immunomodulating protein.

Many other mutant viruses can be made on the basis of deletion or other inactivation (for example) of the following essential genes in the following viruses and virus types:

In herpes simplex viruses, essential genes such as gB, gD, gL, ICP4, ICP8 and/or ICP27 can be deleted or otherwise inactivated as well as or instead of the gH gene used in the above examples. In other herpesvirus, known essential genes, such as any known essential homologues to the gB, gD, gL, gH, ICP4, ICP8 and/or ICP27 genes of HSV, can be selected for deletion or other inactivation. Cytomegalovirus can e.g. be genetically disabled by deleting or otherwise activating genes responsible for temperature-sensitive mutations, for example as identifiable from Dion et al, Virology 158 (1987) 228–230.

In poxvirus such as vaccinia virus, genetically disabled virus can be made by deleting or otherwise inactivating a gene such as one of those identified as essential or as giving rise to conditional-lethal temperature-sensitive mutants, e.g. in Goebel et al, Virology 179 (1990) pp 249 et seq.

Genetically-disable SV40 virus can be made by deleting or otherwise inactivating e.g. the T-antigen encoding region.

Adenovirus type 5 can for example be genetically disable by deleting or otherwise inactivating essential genes such as those identified in the references cited above in the introduction.

These examples can also be applied to uses as mentioned herein.

The examples and embodiments mentioned in the foregoing description and appended claims and more particularly described above are for illustration and not limitation: various modifications in the light thereof will be apparent to persons skilled in the art and are included within the scope of the invention. This disclosure and invention extend to combinations and subcombinations of the features so mentioned, and the present disclosure includes the published documents cited herein, which are hereby incorporated in their entirety by reference.

What is claimed is:

1. A process for treating a tumor in a mammalian subject, the process comprising: administering directly to said tumor a mutant herpesvirus which is defective in respect of a viral gene essential for production of infectious new virus particles and carries heterologous genetic material encoding a cytokine, wherein the cytokine is GM-CSF, said heterologous genetic material being inserted at a site from which said essential herpesviral gene has been completely deleted, so that said mutant virus can infect normal host cells to cause expression therein of said cytokine, but cannot cause production of infectious new virus particles;

wherein said administering results in inhibition of growth of said tumor in said subject.

2. A process according to claim 1, where the genome of said mutant herpesvirus further encodes a heterologous antigen.

3. A process according to claim 1, wherein the mutant herpesvirus has a genome in which an essential gene encoding a viral glycoprotein has been deleted.

4. A process for delivering a gene encoding GM-CSF to cells of a tumor in a mammalian subject and expressing said gene in said cells, wherein said process comprises:

directly injecting into said tumor a mutant herpesvirus which is defective in respect of a viral gene essential for production of infectious new virus particles and carrier heterologous genetic material encoding GM-CSF, said heterologous gentic material being inserted at a site from which said essential herpesviral gene has been completely deleted, so that said mutant virus can infect normal host cells to cause expression therein of GM-CSF, but cannot cause production of infectious new virus particles; wherein said infecting results in delivery of the genetic material encoding GM-CSF to said cells and expression of GM-CSF in said cells of said subject, wherein said expression results in inhibition of growth of said tumor.

5. A method of stimulating a local immune response against a tumor in a tumor-bearing mammalian subject, wherein said method comprises directly administering to said tumor a sufficient amount of a mutant herpesvirus which is defective in respect of a viral gene essential for production of infectious new virus particles and carries heterologous genetic material encoding GM-CSF, said heterologous genetic material being inserted at a site fromm which said essential herpesviral gene has been completely deleted, so that said mutant virus can infect normal host eclls to cause expression therein of GM-CSF, but cannot cause production of infecous new virus particles, wherein said administering stimulates the local immune response against said tumor in said subject, thereby inhibiting the growth of said tumor.

* * * * *

UNITED STATES PATENT AND TRADEMARK OFFICE
CERTIFICATE OF CORRECTION

PATENT NO.    : 6,287,557 B1
DATED         : September 11, 2001
INVENTOR(S)   : Boursnell et al.

It is certified that error appears in the above-identified patent and that said Letters Patent is hereby corrected as shown below:

Column 1,
Line 46, "genese" should read -- genes --.
Line 47, "promote" should read -- promoter --.

Column 2,
Line 17, "E6 E7" should read -- E6 and E7 --.
Line 49, "after" should read -- often --.
Line 55, "Virogentics" should read -- Virogenetics --.

Column 7,
Line 9, "FANTES" should read -- RANTES --.
Line 13, "B7.1. B7.2." should read -- B7.1, B7.2, --.

Column 9,
Line 43, "the side" should read -- the site --.
Line 54, "expressions" should read -- expression --.

Column 10,
Line 65, "text" should read -- next --.

Column 11,
Line 4, "screening of" should read -- screening for --.
Line 55, "does" should read -- dosed --.

Column 12,
Line 22, "solution of" should read -- solution to --.
Line 34, "re-stimulated" should read -- re-stimulation --.

Column 13,
Line 29, "Jan.Feb" should read -- Jan-Feb --.

Column 14,
Line 9, "as in" should read -- as an --.
Line 18, "GH-CSF" should read -- GM-CSF --.

UNITED STATES PATENT AND TRADEMARK OFFICE
CERTIFICATE OF CORRECTION

PATENT NO. : 6,287,557 B1
DATED : September 11, 2001
INVENTOR(S) : Boursnell et al.

It is certified that error appears in the above-identified patent and that said Letters Patent is hereby corrected as shown below:

Column 15,
Line 14, "The 4'" should read -- The 5' --.
Line 24, "pIMM824" should read -- pIMMB24 --.
Line 36, "GTGGAGACTCGAATAATCGCGAGC" should read
-- GTGGAGACGCGAATAATCGCGAGC --.
Line 46, "HSV-2gH" should read -- HSV-2 gH --.
Line 58, "9SC16gH)" should read -- (SC16gH) --.
Line 64, "follows;" should read -- follows: --.

Column 16,
Line 10, "MB91" should read -- MB97 --.
Line 43, "MB-57" should read -- MB57 --.
Line 51, "pIMMB846" should read -- pIMMB46 --.

Column 18,
Line 13, "CD56" should read -- CE56 --.
Line 27, "CGGCCCCCAG" should read -- CGGCCGCCAG --.
Line 30, "ATGCCCACGAGA" should read -- ATGGCCCACGAGA --.

Column 19,
Line 55, "sits" should read -- sites --.
Line 61, "names" should read -- named --.

Column 20,
Line 20, "VS40-lacZ" should read -- SV40-lacZ --.

Column 21,
Line 15, "his" should read -- this --.
Line 54, "Gm-CSF" should read -- GM-CSF --.

UNITED STATES PATENT AND TRADEMARK OFFICE
CERTIFICATE OF CORRECTION

PATENT NO.    : 6,287,557 B1
DATED         : September 11, 2001
INVENTOR(S)   : Boursnell et al.

It is certified that error appears in the above-identified patent and that said Letters Patent is hereby corrected as shown below:

Column 22,
Line 2, "IL-3into" should read -- IL-3 into --.
Line 20, "e" should read -- be --.
Line 40, "describe din" should read -- described in --.
Line 40, "se" should read -- see --.
Line 43, "4037" should read -- 4307 --.
Line 62, "sued" should read -- used --.
Line 63, "IL-2can" should read -- IL-2 can --.

Column 24,
Line 13, "disable" should read -- disabled --.
Line 16, "disable" should read -- disabled --.

Column 35,
Line 35, "carrier" should read -- carries --.

Column 36,
Line 28, "fromm" should read -- from --.
Line 30, "eclls" should read -- cells --.
Line 32, "infecious" should read -- infectious --

Signed and Sealed this

Twenty-fourth Day of June, 2003

JAMES E. ROGAN
*Director of the United States Patent and Trademark Office*